US008592347B2

(12) United States Patent
Frendéus

(10) Patent No.: US 8,592,347 B2
(45) Date of Patent: Nov. 26, 2013

(54) METHOD FOR SCREENING ANTI-LIGAND LIBRARIES FOR IDENTIFYING ANTI-LIGANDS SPECIFIC FOR DIFFERENTIALLY AND INFREQUENTLY EXPRESSED LIGANDS

(75) Inventor: Björn Frendéus, Lund (SE)

(73) Assignee: BioInvent Internatioal AB, Lund (SE)

( * ) Notice: Subject to any disclaimer, the term of this patent is extended or adjusted under 35 U.S.C. 154(b) by 1661 days.

(21) Appl. No.: 10/526,695

(22) PCT Filed: Sep. 3, 2003

(86) PCT No.: PCT/EP03/09991
§ 371 (c)(1),
(2), (4) Date: Mar. 8, 2006

(87) PCT Pub. No.: WO2004/023140
PCT Pub. Date: Mar. 18, 2004

(65) Prior Publication Data
US 2006/0199219 A1      Sep. 7, 2006

(30) Foreign Application Priority Data
Sep. 4, 2002 (GB) .................................. 0220506.0

(51) Int. Cl.
*C40B 20/02* (2006.01)
*C40B 20/04* (2006.01)
*C40B 20/06* (2006.01)
*C40B 20/08* (2006.01)
*C40B 30/04* (2006.01)

(52) U.S. Cl.
USPC ................. 506/9; 506/3; 506/4; 506/5; 506/6

(58) Field of Classification Search
USPC ............................................. 506/3, 4, 5, 6, 9
See application file for complete search history.

(56) References Cited

U.S. PATENT DOCUMENTS

| 5,366,862 | A  | * | 11/1994 | Venton et al. | ................. | 435/7.1 |
| 5,688,507 | A  | * | 11/1997 | Weitz et al. | ................. | 424/184.1 |
| 6,794,128 | B2 | * | 9/2004  | Marks et al. | ................. | 435/5 |
| 7,135,287 | B1 | * | 11/2006 | Lonberg et al. | ................. | 435/6 |

FOREIGN PATENT DOCUMENTS

| WO | WO 91/18980 | 12/1991 |
| WO | WO 00/52054 | 9/2000 |
| WO | WO 02/39120 | 5/2002 |

OTHER PUBLICATIONS

Mandecki et al., 1995, A Mathmatical Model for Biopanning (Affinity Selection) Using Peptide Libraries on Filamentous Phage, J. Theor. Biol., 176: 523-530.*
scienceworld.wolfram.com, Law of Mass Action, 3 pages, printed Mar. 10, 2010.*
Barbas CF, Kang As, Lerner RA and Benkovic SJ, (1991), Proc. Natl. Acad. Sci. USA 88, 7978/7982.
Carlsson, R., Fischer, H. and Sjogren, H.O. (1988) J. Immunol 140, 2484.
Chiswell DJ and McCafferty J. (1992), Trends Biotechnol. 10, 80-84.
Clackson T, Hoogenboom HR, Griffiths AD and Winter G, (1991), Nature 352, 624-628.
de Kruif, J., Terstappen, L., Boel, E. and Logtenberg, T (1995) Proc Natl. Acad. Sci. USA 92, 3938.
Felici F. Luzzago A. Manaci P. Nicosia A, Sollazzo M. and Traboni C, (1995), biotechnol. Annual Rev. 1, 149-183.
Francisco, J.A., Stathopoulous, C., Warren, R.A., Kilburn, D.G. and Georgiou, G. (1993) Biotechnology (NY) 11, 491.
Gao, C., Lin, C.H., Lo, C.H., Mao, S., Wirsching, P., Lerner, R.A. and Janda, K.D. (1997) Proc Natl Acad Sci USA 94, 11777.
Hanes, J. and Pluckthun, A. (1997) Proc Natl Acad Sci USA 94, 4937.
He, M. and Taussing, M.J. (1997) Nucleic Acids Res. 25, 5132.
Hoogenboom HR and Winter G. (1992), J. Mol. Biol. 227, 381-388.
Hoogenboom HR, deBruine AP, Hutton SE, Hoct RM, Arends JW and Rooves RC, (1998), Immunotechnology 4(1), 1-20.
Huls, G.A., Heijenen, I.A., Cuomo, M.E., Koningsberger, J.C., Wiegman, L., Boel, E., van der Vuurst de Vries, A.R., Loyson, S.A., Helfrich, W., van Berge Henegouwen, G.P., van Meijer, M., de Kruif, J. and Logtenberg, T., (1999) Nat Biotechnology 17, 276.
Jacobsson, K. and Frykberg, L., (1995) Biotechniques 18, 878.
Katz BA, (1997), Annual Rev. Biophys. Biomol. Struct. 26, 27-45.
Kay BK and Paul JI, (1996), Mol. Divers. 1, 139-140.
Koide, A., Bailey, C.W., Huang, X. and Koide, S. (1998) J. Mol. Biol. 284, 1141.
Markland, W., Roberts, B.L., Saxena, M.J., Guterman, S.K. and Ladner, R.C. (1991) Gene 109, 13.

(Continued)

Primary Examiner — Amber D Steele
(74) Attorney, Agent, or Firm — Kenyon & Kenyon LLP

(57) ABSTRACT

The present invention relates to screening methods and, in particular, to methods of screening anti-ligands libraries for identifying anti-ligands specific for differentially and/or infrequently expressed ligands. The method comprises the steps of providing a library of anti-ligands; providing a first subtractor ligand; providing a second target ligand; determining the amount of the first and second target ligands using one or more equations derived from the universal law of mass action; providing the determined amount of a first subtractor ligand; providing the determined amount of a second target ligand; providing separation means capable of use to isolate anti-ligand bound to the second target ligand from anti-ligand bound to the first subtractor ligand; exposing the library of to the first and second target ligands to permit binding of anti-ligands to ligands; and using the separation means to isolate the anti-ligand bound to second target ligand.

22 Claims, 10 Drawing Sheets

(56) References Cited

OTHER PUBLICATIONS

Figure 1:
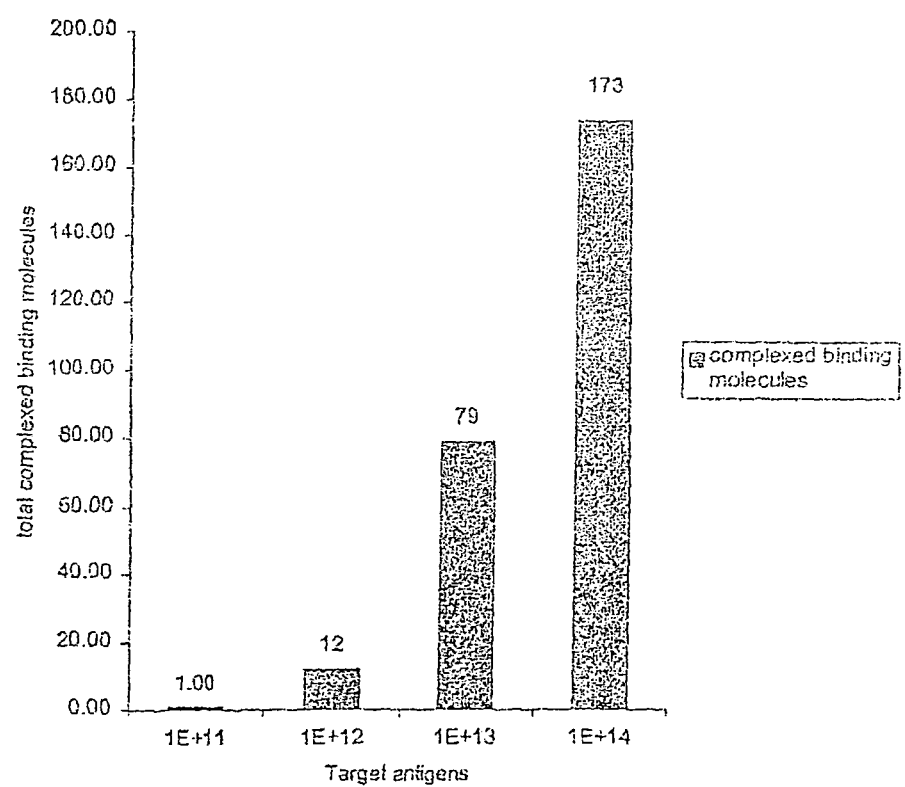

Marks JD, Hoogenboom HR, Bonnert TP, McCafferty J, Griffiths AD and Winter G, (1991), J. Mol. Biol. 222, 581-597.

Mattheakis, L.C., Bhatt, R.R. and Dower, W.J. (1994) Proc Natl Acad Aci USA 91, 9022.

McCafferty, J., Griffiths, AD., Winter, G. and Chiswell, D.J. (1990) Nature 348, 552.

Siegel, D.L., Chang, T.Y., Russell, S.L. and Bunya, V.Y. (1997) J. Immunol Methods 206, 73-85.

Smith, G.P. (1985) Science 28, 1315.

Smith, G.P. and Scott, J.K. (1993) Methods Enzymol. 217, 228.

Stahl, S., Sjolander, A., Nygren, P.A., Berzins, K., Perlmann, P. and Uhlen, M. (1989) J Immunol Methods 124, 43.

Weng, S., Gu, K., Hammond, P.W., Lohse, P., Rise, C., Wagner, R.W., Wright, M.C. and Kuimelis R.G. (2002) Proteomics 2, 48.

Winter, G., Griffiths, A.D., Hawkins, R.E. and Hoogenboom, H.R. (1994)Annu Rev Immunol 12, 433.

Kay, Winter and McCafferty (1996) Phage display of pepti8des and protens: a laboratory manual Ed Kay, Academic Press, Inc. ISBN 0-12-402380-0.

Rodi et al., (1999) J. Mol. Biol. 285 p. 197-203.

Stausbol-Gron, Brian, et al., "De Novo Identification of cell-type specific antibody-antigen paris by phage display subtraction. Isolation of a Human single chain antibody fragment against human keratin 14" Eur. J. Biochem., vol. 268, pp. 3099-3107, 2001.

Stausbol-Gron, Brian, et al., "A model phage display subtraction method with potential for analysis of differential gene expression" FEBS Letters, vol. 391, pp. 71-75, 1996.

Mandecki, Wlodek, et al., "A Mathematical Model for Biopanning (Affinity Selection) Using peptide Libraries on Filamentous Phage", J. Theor. Biol., vol. 176, pp. 523-530, 1995.

Williams, Brent R., et al., "Polyclonal anti-colorectal cancer Fab phage display library selected in one round using density gradient centrifugation to separate antigenbound and free phage", Immunology Letters, vol. 81, pp. 141-148, 2002.

Lou et al. "Antibodies in Haystacks: How Selection Strategy Influences the Outcome of Selection from Molecular Diversity Libraries." Journal of Immunological Methods 253: 233-242 (2001).

Pluckthun et al. "In Vitro Selection and Evolution of Proteins." Advances in Chemistry 55: 367-403 (2001).

Schwab et al. "Caveats for the Use of Surface-Adsorbed Protein Antigen to Test the Specificity of Antibodies." Journal of Immunological Methods 147: 125-134 (1992).

\* cited by examiner

METHOD FOR SCREENING ANTI-LIGAND LIBRARIES FOR IDENTIFYING ANTI-LIGANDS SPECIFIC FOR DIFFERENTIALLY AND INFREQUENTLY EXPRESSED LIGANDS

RELATED APPLICATION

This application claims priority of and is the U.S. national phase application of PCT/EP2003/009991, filed Sep. 3, 2003, which further claims priority of Great Britain Application No. 0220506.0, filed Sep. 4, 2002.

The present invention relates to screening methods and, in particular, to methods of screening anti-ligand libraries for identifying anti-ligands specific for differentially and/or infrequently expressed ligands.

Protein or peptide based libraries are often used for selection of anti-ligand molecules with specificity for certain ligands.

Such libraries are constructed so that the protein molecule is, in some manner, physically linked to the genetic information encoding the particular protein molecule. The protein molecule is thus displayed together with its gene.

Commonly used display formats rely on cell or virus host particles to present the protein molecule; and include bacterial display (Francisco et al., 1993) and phage display (Smith, 1995; Smith and Scott, 1993; Winter et al., 1994). Such systems display the potential anti-ligand molecule on the surface of the host particle, whilst the genetic information for the displayed molecule is harboured inside the particle and said methods have been employed successfully for selection of specific protein based anti-ligands.

Other display formats relying on in vitro translation exist; including various forms of ribosome display (Mattheakis et al., 1994; Hanes and Pluckthun, 1997; He and Taussig, 1997) that rely on non-covalent linkage of the genetic information to the protein molecule; and other display formats also relying on in vitro translation, whereby a covalent linkage exists between the genetic information and the potential anti-ligand protein molecule, e.g. the Profusion (Weng et al., 2002) or the Covalent Display Technology (Gao et al., 1997).

The displayed peptide or proteinaceous anti-ligand libraries may be totally randomised, e.g. when peptide libraries are used, or they may be based on a constant region scaffold structures incorporating a further structure conferring variability.

Scaffold structures often used are based on the antibody heavy and light chain variable domains (McCafferty et al., 1990) but may also be based on other scaffolds such as fibronectin (Jacobsson and Frykberg, 1995; Koide et al., 1998), protein A domains (Stahl et al., 1989), or small stable protein domains e.g. BPTI (Markland et al., 1991).

Selection of anti-ligands exhibiting a certain binding specificity, from display libraries, is often performed using so called "biopannig" methods.

The target ligand may be immobilised on a solid surface and specific anti-ligand members of a library are exposed to the immobilised target ligand to enable the anti-ligands of interest to bind to the target ligand. Unbound library members are subsequently washed away and the anti-ligands of interest are retrieved and amplified.

Proteinaceous particles other than the members of the anti-ligand library, e.g. phage expressing antibody fragments, may be "sticky" resulting in the binding and isolation of some non-target specific molecules. Non-specific binding may be minimised by adding certain compounds to the anti-ligand display construct/ligand mixture in order to act as blocking agents to reduce this background binding of non-specific anti-ligands e.g. milk, bovine serum albumin, serum (human/foetal calf), gelatine and for certain (non-cellular) applications, detergent.

A number of washing procedures have been devised to reduce non-specific binding of library members to cells and to aid separation of cells from contaminating and/or non-specifically bound library members.

Such methods include washing of cells magnetically fixed in a column (Siegel et al., 1997), in order to minimise shearing forces and to allow rebinding of dissociated phage. Another method of washing cells is by centrifugation in a higher density medium such as Ficoll or Percoll, in order to selectively remove non-specific and low affinity anti-ligands and further spatially separate cells and cell-bound anti-ligands from free-anti-ligands and non-specifically bound anti-ligands (Carlsson et al., 1988; Williams and Sharon, 2002).

Depending on the efficiency of the selection process, several rounds of panning may be required to eliminate or at least sufficiently reduce non-specific anti-ligands to a desirable level (Dower et al, 1991).

In another selection method, the target ligand(s) binds the specific anti-ligand library members whilst in solution. Bound anti-ligands are then isolated using, for example, a retrievable tag attached to the target ligand. The most commonly used tag is biotin, which permits the complex between target molecule and displayed specific library member to be retrieved using avidin coupled to a solid support e.g. a magnetic bead (Siegel et al, 1997).

These methods are used when the target ligand is well known and available in a purified form. Selections against a single target ligand at a time are routine. Selection for several defined target ligands may be performed simultaneously. Target ligands may be one or more of small haptens, proteins, carbohydrates, DNA and lipids.

For many applications, specific anti-ligands against differentially expressed ligands are of interest. For example, proteins may be differentially expressed on cells and tissue derived from patients with disease, when compared to those from healthy controls. Such diseases include microbial, viral, or parasitic infections, asthma, chronic inflammatory and autoimmune disorders, cancer, neurological-, cardiovascular-, or gastrointestinal disease. Similarly, the protein composition of body fluids, e.g. plasma, cerebrospinal fluid, urine, semen, saliva and mucous, may differ between patients with disease compared to healthy controls.

Consequently, besides their general applicability as research tools to identify differentially expressed ligands, anti-ligands specific for differentially expressed ligands may be used as tools for use in the diagnosis, prevention and/or treatment of disease.

Recent advances within the genomics and proteomics fields have indicated the presence of a multitude of as yet undefined differentially expressed molecules, stressing the importance of methods for generation of specific anti-ligands for these potential target ligands.

Many of these differentially expressed molecules are expected to be present on cell surfaces and thereby constitute potential targets for targeted therapies using, e.g., specific antibodies which may be conjugated to bioactive (e.g. cytotoxic) agents.

Large and highly diversified anti-ligand display libraries provide methods of isolating anti-ligands with specificity to unknown cellular ligands of carbohydrate, protein, lipid, or combined actions thereof.

Biopanning processes currently available include whole-cell, cell-portion, and cell membrane based methods that, in principle, permit isolation of display constructs exhibiting anti-ligands specific to cell membrane ligands in their native configuration. However, the success in isolating anti-ligands against differentially expressed ligands or cell sub-population specific ligands (de Kruif et al., 1995) has been limited, and rational means of designing experiments to succeed in this task have been absent.

Furthermore, selection for anti-ligands to ligands that differ between two groups of ligand populations, e.g. normal and transformed cells, have primarily isolated those anti-ligands with specificity against certain highly expressed ligands uniquely expressed on the target cell, e.g. the tumour antigen Ep-CAM-1 (as extensively reported in the literature e.g. Huls et al., 1999). It has been difficult to produce specific anti-ligands towards ligands expressed at a low level or those that are differentially expressed.

Presently known methods of selecting and isolating binders to specific antigens are not able to isolate binders for antigens expressed in two different samples but at different levels of expression. Furthermore, presently known methods do not attempt to optimise the experimental conditions for the biopanning reaction e.g. the reduction of biopanning rounds or reagents used.

Stausbøl-Grøn et al. (1996) teaches the enrichment of binders possessing a specificity for antigen uniquely distributed in one sample and therefore absent from a second sample.

Stausbøl-Grøn et al. (2001) also teaches the enrichment of binders possessing a specificity for antigen uniquely distributed in one sample and absent from another. This document represents a continuation of the earlier study. In this study the enrichment method has been altered to use a polyclonal serum to mask commonly expressed antigens. However, this serum would also mask the common antigens present at different concentrations in the two samples i.e. the differentially expressed antigens.

WO 00/52054 (Genentech) teaches the isolation of binders with specificity to Decay accelerating factor (CD55).

Therefore, the present invention seeks to provide more efficient and faster screening methods which remove or mitigate the aforementioned problems associated with conventional screening methods.

The invention makes possible: (i) isolation of binders specific for differentially expressed ligands, including ligands that are expressed and upregulated at low levels in one ligand population compared to another; and (ii) differential analysis of ligand abundance at ligand level, independent of ligand nature (e.g. carbohydrate, protein, nucleotide, lipid or a conjugate thereof).

According to the invention there is provided a method of isolating an anti-ligand to at least one target ligand comprising the steps of:
(i) providing a library of anti-ligands;
(ii) providing an amount of a first subtractor ligand;
(iii) providing an amount of a second target ligand;
(iv) determining amounts of the first subtractor and second target ligands using one or more equations derived from the universal law of mass action $$\frac{[C]^c[d]^d}{[A]^a[B]^b} = K_{eq},$$

so as to permit isolation of at least one anti-ligand to at least one target ligand;
(v) providing the amount of a first subtractor ligand determined in step (iv);
(vi) providing the amount of a second target ligand determined in step (iv);
(vii) providing separation means for isolating anti-ligand bound to the second target ligand from anti-ligand bound to the first subtractor ligand;
(viii) exposing the library of (i) to the ligands of (v) and (vi) to permit binding of anti-ligands to ligands; and
(ix) using the separation means to isolate the anti-ligand bound to second target ligand.

It is not intended that the steps of the invention necessarily have to be performed in any specific order.

By "providing the determined amount" we include the meaning of providing an amount of ligand that was already known such that the equations of the invention have been used to verify that the known amount provided is suitable for isolating the desired anti-ligand(s).

The reaction parameters that are utilised for a given selection process may be optimised according to the present invention by calculations applying the Mass Law of Action and equations derived therefrom, and taking parameters such as molecular library diversity, anti-ligand copy number, desired detection limit of upregulation, desired anti-ligand affinity, and ligand concentration into consideration.

The invention also provides the method of isolating at least one anti-ligand to at least one target ligand comprising the steps of:
(i) providing data set(s) describing a library of anti-ligands;
(ii) providing data set(s) describing a first subtractor ligand;
(iii) providing data set(s) describing a second target ligand;
(iv) automatically determining an amount of the first subtractor and second target ligands using, one or more equations derived from the universal law of mass action $$\frac{[C]^c[d]^d}{[A]^a[B]^b} = K_{eq},$$

(v) providing the amount of the first subtractor ligand determined in step (iv);
(vi) providing the amount of the second target ligand determined in step (iv);
(vii) providing the library of anti-ligands described by the data-set of step (i);
(viii) providing separation means for isolating anti-ligand bound to the second target ligand from anti-ligand bound to the first subtractor ligand;
(ix) exposing the library of (vii) to the ligands of (v) and (vi) to permit binding of anti-ligands to ligands; and
(x) using the separation means to isolate the anti-ligand bound to second target ligand.

Step (iv) and at least one of steps (v), (vi), (vii) (ix) and (x) may be performed automatically.

Preferably, the method also provides the further step of releasing the anti-ligand from the second target ligand for isolation and further use.

Steps (ii) to (i) may be repeated one or more times, if necessary, in order to further refine the purity of the anti-ligand isolate.

It is preferable that the invention provides one of the first subtractor or second target ligand in an amount that is in excess, in comparison to the other ligand.

Preferably the excess of ligand is between 10 and 1000 fold.

The magnitude of excess of subtractor ligand population determines the highest-possible "resolution" (i.e. how well you are able to discriminate between anti-ligands with specificity for ligands that are low upregulated, moderately upregulated, highly upregulated, or uniquely expressed) that you will be able to detect, and how well you will be able to discriminate between differently expressed ligands. For example, if you are using a library with 100 target ligand specific anti-ligands and you acid large enough concentrations of positive ligand so that all anti-ligand will be bound to ligand at equilibrium, then a subtractor ligand population excess of 10-fold will allow you to reduce the frequency of anti-ligands with specificity for commonly expressed ligands by 90%, whereas a 200-fold excess (twice the number of anti-ligand specific binders) would allow you to remove common binders (see FIG. 5 and the very last paragraph of example 4).

The separation means of the first subtractor and/or second target ligands are preferably at least one selected from a solid support, cell membrane and/or portions thereof, synthetic membrane, beads, chemical tags and free ligand in solution.

Yet more preferably the separation means are cell membranes and/or portions thereof.

Even more preferably, the first subtractor and second target ligands are fixed to or incorporated within separation means of different densities.

Most preferably the first subtractor ligand has separation means comprising a membrane vesicle, and the second target ligand has a separation means comprising a whole cell membrane.

Preferably the method of separation is one of density centrifugation (Williams and Sharon, 2002), solid support sequestration, magnetic bead sequestration (Siegel et al., 1997), chemical tag binding and aqueous phase partitioning.

More preferably the method of separation is density centrifugation performed on a density gradient e.g. Ficoll; Percoll; iodinated gradient media, wherein during centrifugation, the first and second target ligands move through the Ficoll gradient to differing extents whereby the first and second target ligands can be isolated from their differing end points.

Most preferably the method of separation uses a sucrose-polymer gradient e.g. Ficoll.

Preferably the screened library is a display library whereby the anti-ligand of interest is expressed by and displayed on the surface of a library member. Most preferably the library is a phage display library wherein the anti-ligand is displayed on the surface of a bacteriophage.

The display of proteins and polypeptides on the surface of bacteriophage (phage), fused to one of the phage coat proteins, provides a powerful tool for the selection of specific ligands. This 'phage display' technique was originally used by Smith in 1985 to create large libraries of antibodies for the purpose of selecting those with high affinity for a particular antigen. More recently, the method has been employed to present peptides, domains of proteins and intact proteins at the surface of phage in order to identify ligands having desired properties.

The principles behind phage display technology are as follows:
(i) Nucleic acid encoding the protein or polypeptide for display is cloned into a phage;
(ii) The cloned nucleic acid is expressed fused to the coat-anchoring part of one of the phage coat proteins (typically the p3 or p8 coat proteins in the case of filamentous phage), such that the foreign protein or polypeptide is displayed on the surface of the phage;
(iii) The phage displaying the protein or polypeptide with the desired properties is then selected (e.g. by affinity chromatography) thereby providing a genotype (linked to a phenotype) that can be sequenced, multiplied and transferred to other expression systems.

Alternatively, the foreign protein or polypeptide may be expressed using a phagemid vector (i.e. a vector comprising origins of replication derived from a phage and a plasmid) that can be packaged as a single stranded nucleic acid in a bacteriophage coat. When phagemid vectors are employed, a "helper phage" is used to supply the functions of replication and packaging of the phagemid nucleic acid. The resulting phage will express both the wild type coat protein (encoded by the helper phage) and the modified coat protein (encoded by the phagemid), whereas only the modified coat protein is expressed when a phage vector is used.

The use of phage display to isolate ligands that bind biologically relevant molecules has been reviewed in Felici et al. (1995), Katz (1997) and Hoogenboom et al. (1998). Several randomised combinatorial peptide libraries have been constructed to select for polypeptides that bind different targets, e.g. cell surface receptors or DNA (Kay and Paul, (1996)).

Proteins and multimeric proteins have been successfully phage-displayed as functional molecules (see Chiswell and McCafferty, (1992)). In addition, functional antibody fragments (e.g. Fab, single chain Fv [scfv]) have been expressed (McCafferty et al. (1990); Barbas et al. (1991); Clackson et al. (1991)), and some of the shortcomings of human monoclonal antibody technology have been superseded since human high affinity antibody fragments have been isolated (Marks et al. (1991) and Hoogenboom and Winter (1992)).

Further information on the principles and practice of phage display is provided in *Phage display of peptides and proteins: a laboratory manual* Ed Kay, Winter and McCafferty (1996), the disclosure of which is incorporated herein by reference.

Preferred subtractor and target ligands include antigens, receptor ligands, and enzyme targets that comprise at least one from carbohydrate, protein, peptide, lipid, polynucleotide, inorganic molecules and conjugated molecules.

Preferred anti-ligands making up the anti-ligand library of the invention include antibodies, and antigen binding variants, derivatives or fragments thereof; scaffold molecules with engineered variable surfaces; receptors; and enzymes.

Further preferably, the ligand and its separation means are exposed to a stimulus which influences the expression of target ligands on said ligand constructs, in order to investigate the anti-ligands specific for changes in ligand expression in given situations.

Selected anti-ligands identified by the invention may subsequently be used in the manufacture of a pharmaceutical composition for use in medicine for the treatment, imaging, diagnosis or prognosis of disease. Anti-ligands based on antibodies and most importantly on human antibodies have great therapeutic potential.

A further aspect of the invention, is exemplified by the use of computerised means to perform the method of the invention, and further includes a computer program product, comprising a computer readable medium having thereon computer program code means adapted, when said program is loaded onto a computer, to make the computer execute the procedure of the method.

Additionally the invention includes a computer program, distributable by electronic data transmission, comprising computer program code means adapted, when said program is loaded onto a computer, to make the computer execute the procedure of the method.

DEFINITIONS

By "biopanning" we mean a method of selection of one member from a desired anti-ligand-ligand-binding pair, based on its ability to bind with high affinity to the other member.

By "ligand" we include the meaning of one member of a ligand/anti-ligand binding pair. The ligand may be, for example, one of the nucleic acid strands in a complementary hybridised nucleic acid duplex binding pair; an effector molecule in an effector/receptor binding pair; or an antigen in an antigen/antibody or antigen/antibody fragment binding pair.

By "anti-ligand" we include the meaning of the opposite member of a ligand/anti-ligand binding pair. The anti-ligand may be the other of the nucleic acid strands in a complementary, hybridised nucleic acid duplex binding pair; the receptor molecule in an effector/receptor binding pair; or an antibody or antibody fragment molecule in antigen/antibody or antigen/antibody fragment binding pair, respectively.

By "antigen" we include the meaning a molecule or chemical compound that is able to interact with antibodies but not necessarily produce an immune response. Such antigens include, but are not limited to molecules of protein, peptide, nucleotide, carbohydrate, lipid or a conjugate thereof.

By "differentially expressed ligands" we mean ligands that are either expressed at differing levels between the target and subtractor sources, including those expressed only in certain conditions/places and not in others; or where either the target or subtractor ligand is a modified version of the other from the target and subtractor ligands. For example, some antigens are highly expressed on the cell surfaces of diseased cells (e.g. cancer cells and at low levels or not at all on the equivalent healthy cells (e.g. non-cancerous cells).

By "low expression ligands" we mean those ligands that are expressed at low levels i.e. less than 20,000 copies per cell (this includes most wild-type expressed cell surface receptors) or ligands occurring at a frequency of less than 1% of any other, more highly expressed ligand in the positive ligand population sample.

By "ligand construct" we mean a system which comprises target and/or subtractor ligand associated with separation means.

The term "antibody variant" shall be taken to refer to any synthetic antibodies, recombinant antibodies or antibody hybrids, such as, but not limited to, a single-chain antibody molecule produced by phage-display of immunoglobulin light and/or heavy chain variable and/or constant regions, or other immunointeractive molecule capable of binding to an antigen in an immunoassay format that is known to those skilled in the art.

The term "antibody derivative" refers to any modified antibody molecule that is capable of binding to an antigen in an immunoassay format that is known to those skilled in the art, such as a fragment of an antibody (e.g. Fib or Fv fragment), or an antibody molecule that is modified by the addition of one or more amino acids or other molecules to facilitate coupling the antibodies to another peptide or polypeptide, to a large carrier protein or to a solid support (e.g. the amino acids tyrosine, lysine, glutamic acid, aspartic acid, cysteine and derivatives thereof, $NH_2$-acetyl groups or COOH-terminal amido groups, amongst others).

By "density centrifugation" we mean the separation of items e.g. cells, organelles and macromolecules, according to their density differences. This separation is achieved by centrifugation using a density gradient of an appropriate solution, through which the items being separated move on the basis of their density.

The "Law of Mass Action" is a universal law of nature that is applicable under any circumstance. This law states that for the reaction:

$$aA+bB \rightarrow cC+dD$$

and if that system is at equilibrium at a given temperature, then the following ratio is a constant:

$$\frac{[C]^c[d]^d}{[A]^a[B]^b} = K_{eq}$$

where:
A, B, C &D=are the participants in the reaction (reactants and products)
a, b, c, & d=the coefficients necessary for a balanced chemical equation
And wherein the constant is calculated in terms of concentration (indicated by [ ]) and K has units $M^{c+d-(a+b)}$.

By "data set(s)" we mean a set of information describing the compound in a form suitable for inputting into a computer for automatic processing of that information. The information provided may, for example, concern the number of anti-ligand molecules.

By "automatic determination" we mean the use of equations derived from the law of mass action, by a computer or other automated device, in order to determine from the provided data, the amounts of ligand necessary to perform the invention

DESCRIPTION OF PREFERRED EMBODIMENTS AND DRAWINGS

Examples embodying certain aspects of the invention shall now be described, with reference to the following figures in which:—

FIG. 1—The capture of anti-ligands complexed to ligand as a function of target ligand density where: Kd=10 nM, Target ligand specific anti-ligand copy number (A)=200, Volume=2.5 ml.

Figure 2:
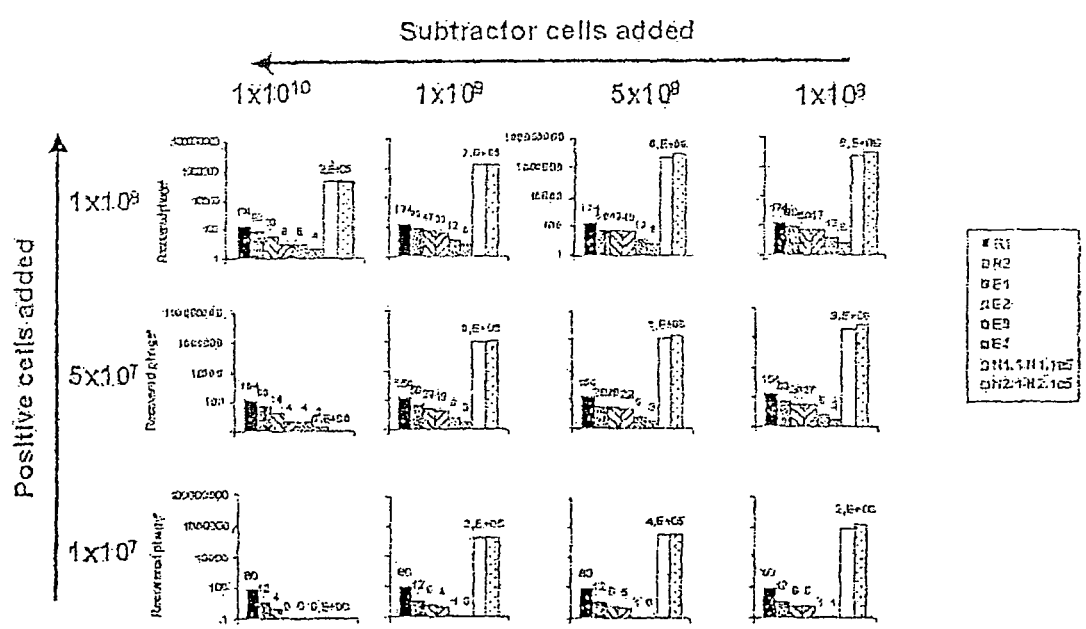

FIG. 2—The anti-ligand molecule capture on target ligand constructs as a function of 1) the number of ligands expressed on the subtractor and target ligand constructs respectively and 2) the number of target and subtractor ligand constricts used in the selection process. The indicated numbers represent the capture of anti-ligands (on target ligand constructs) with specificity for ligands represented in Table I. The reaction parameters Kd=10 nM, target ligand specific anti-ligand copy number T=200 for all anti-ligand specificities, volume (V)=2.5 ml.

Figure 3:
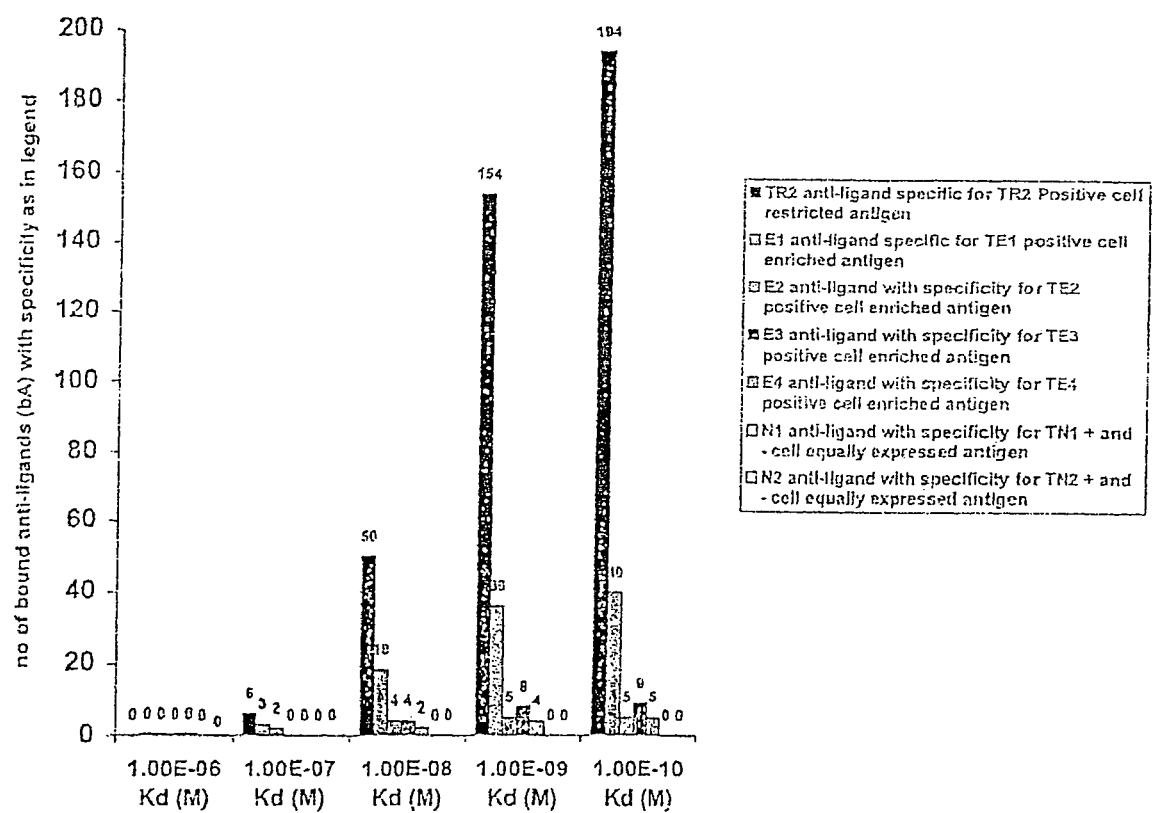

FIG. 3—Anti-ligand capture on target cells as a function of anti-ligand specificity and affinity. Antigen categories are as described in Table 1. Target cell input ($C_p$) is 5×10$^7$, subtractor cell input ($C_s$) is 1010, volume (V) is 2.5 ml and assuming a ligand specific anti-ligand input (A) of 200.

Figure 4:
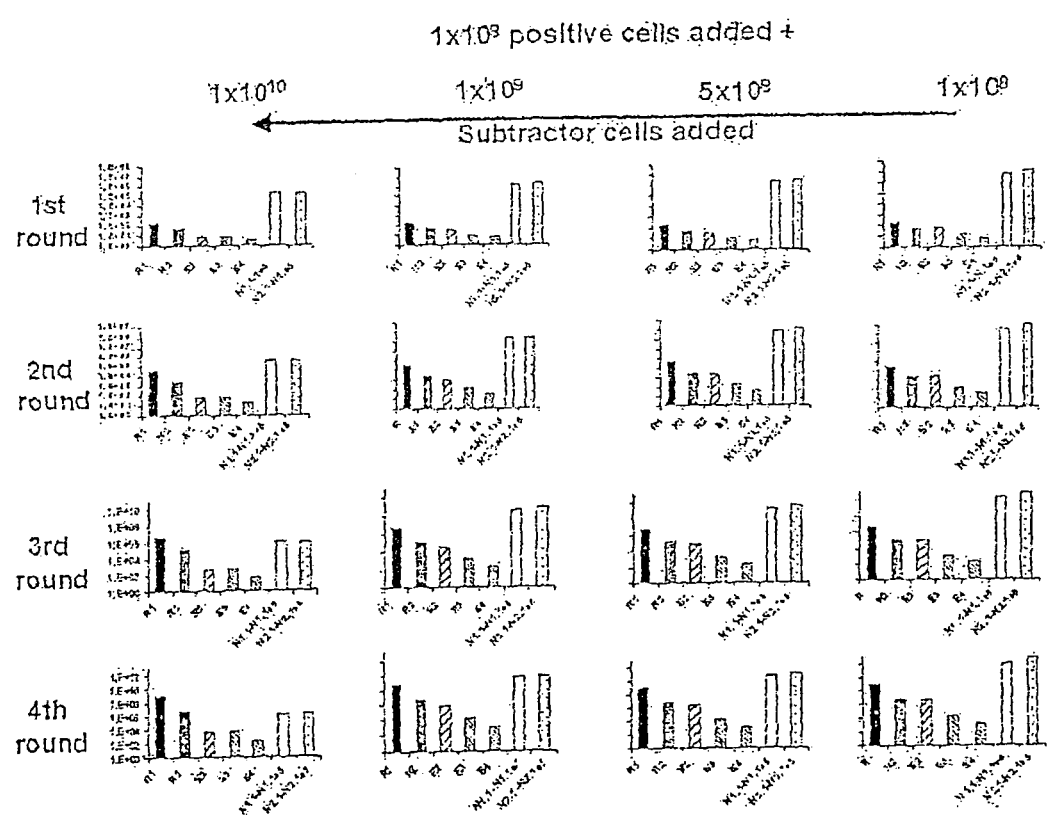

FIG. 4—Histogram showing frequencies of anti-ligand specificity as a function of excess subtractor ligand (cells) added and the number of selection rounds performed. Histograms show the relative numbers of anti-ligands isolated with different specificities. The reaction parameters of FIG. 2 apply.

Figure 5:
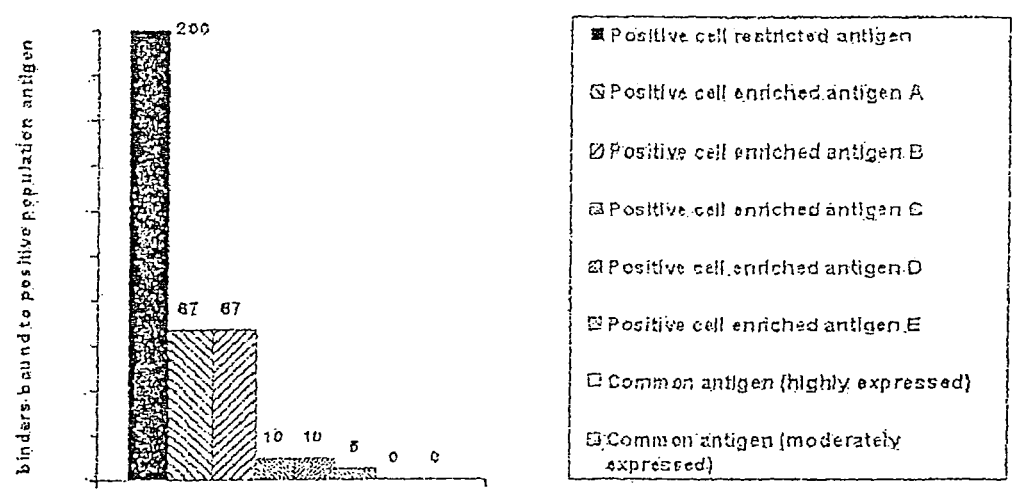

FIG. 5—Target population ligand abundance independent, but target to subtractor ligand population ligand abundance dependent isolation of anti-ligands with specificity for ligands of different abundance within target ligand population and between target and subtractor ligand populations as described in Table 2. The reaction parameters of FIG. 2 apply, and subtractor ligand population excess is ×200 as described in example 4.

Figure 6:
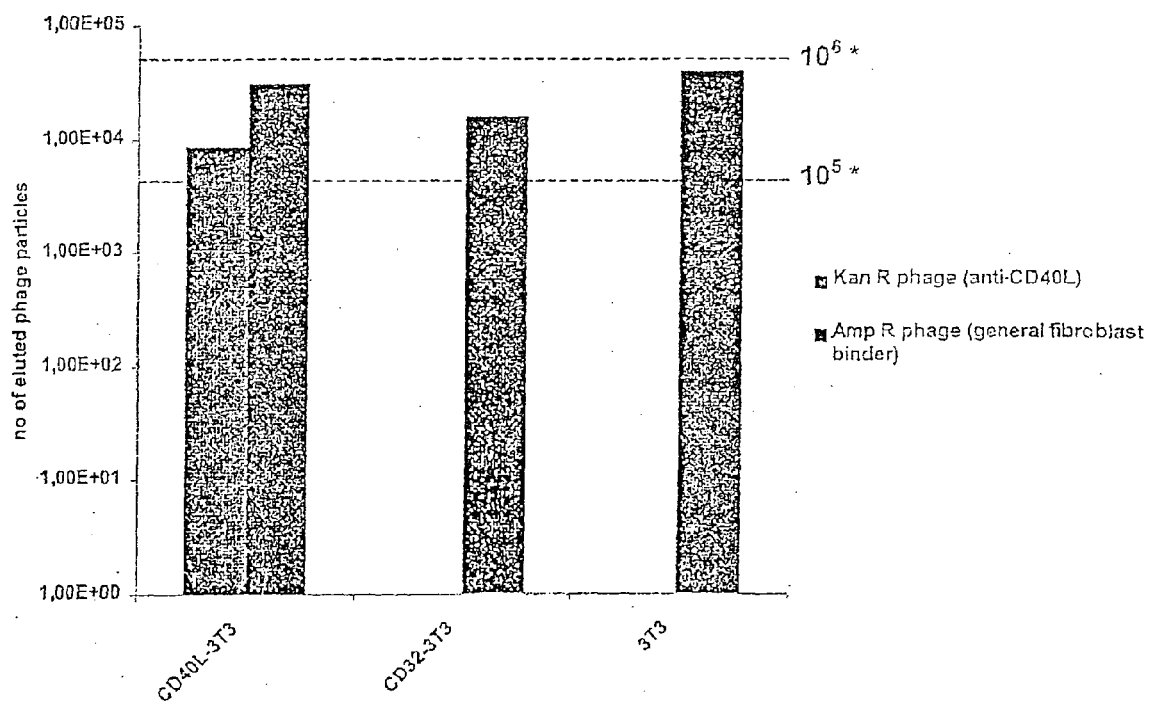

FIG. 6—Elution of CD40L specific phage and general mouse fibroblast binder phage following selection on non-transfected mouse fibroblast cells (3T3), CD32 transfected mouse fibroblast cells (CD32-3T3) or CD40L transfected mouse fibroblast cells (CD40L-3T3). Dotted lines show the theoretical number of CD40L specific phage bound to CD40L-3T3 cells at equilibrium given a CD40L specific phage particle input number of $10^5$ or $10^6$ and parameters used in the selection process.

Figure 7A:
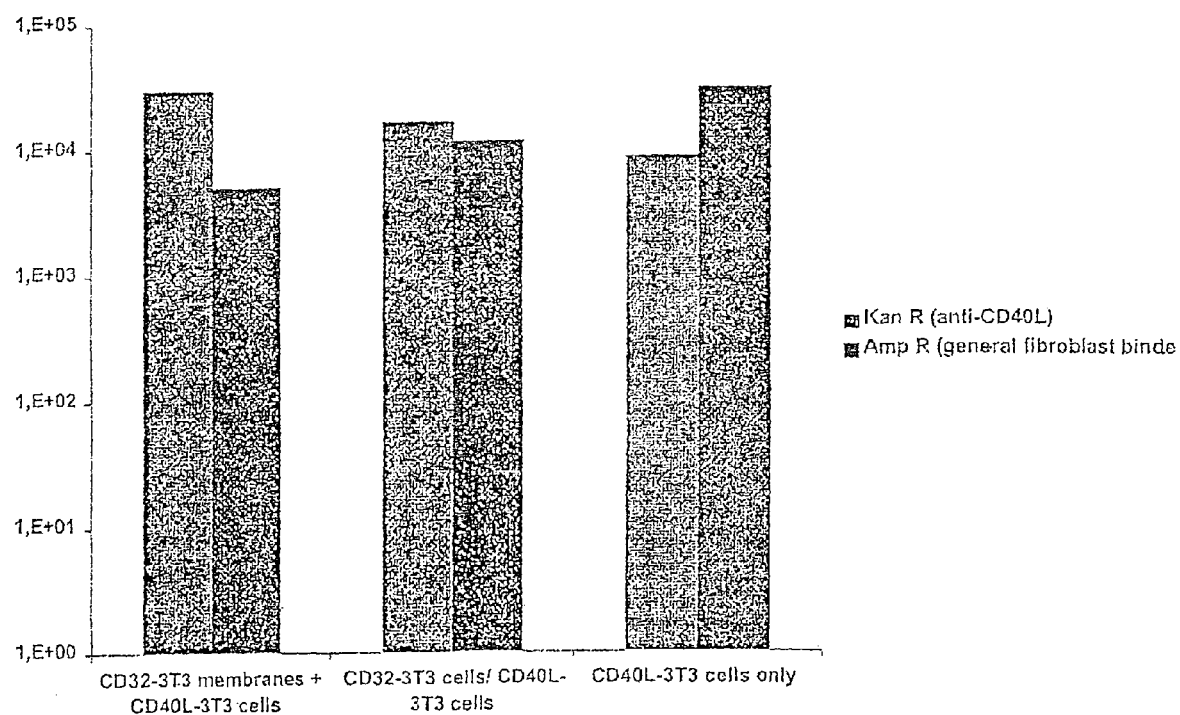
Figure 7B:
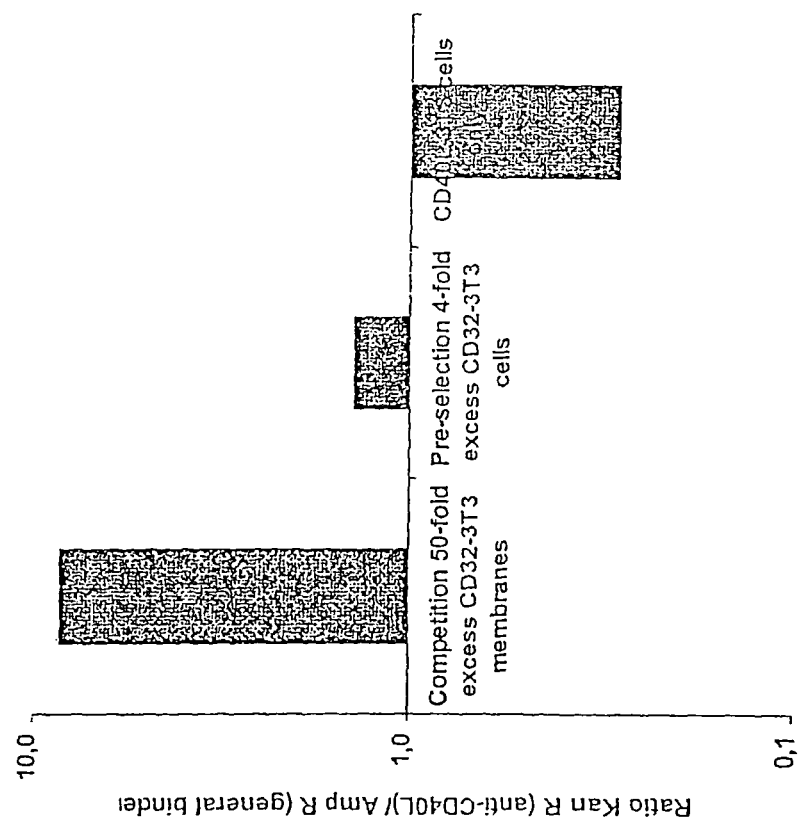

FIG. 7—Numbers (FIG. 7A) and ratios (FIG. 7B) of CD40L specific phage particles to general fibroblast binder phage (determined by cfu after infection of *E. coli* HB101F' and plating on LA plates containing appropriate antibiotics), following selection in absence of subtractor ligands (CD40L-3T3 cells only), pre-selection using a fourfold excess of CD32-transfected 3T3 cells, and pre-selection using a 50-fold excess of cell membranes from CD32 transfected 3T3 cells.

Figure 8A:
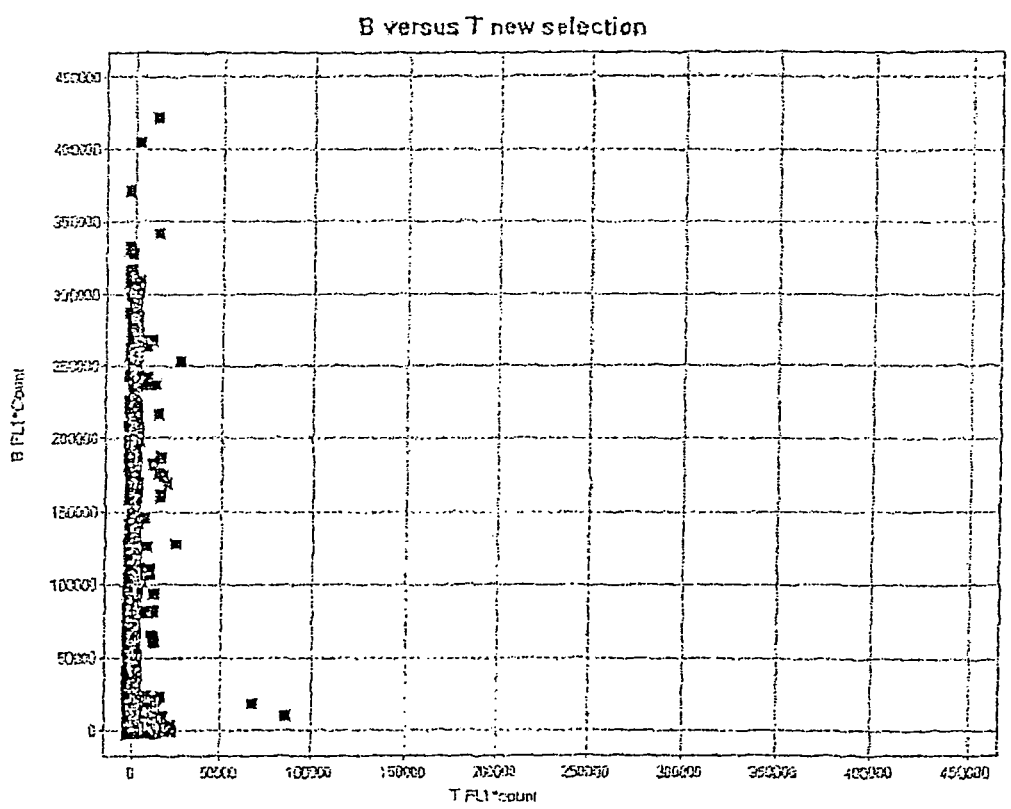
Figure 8B:
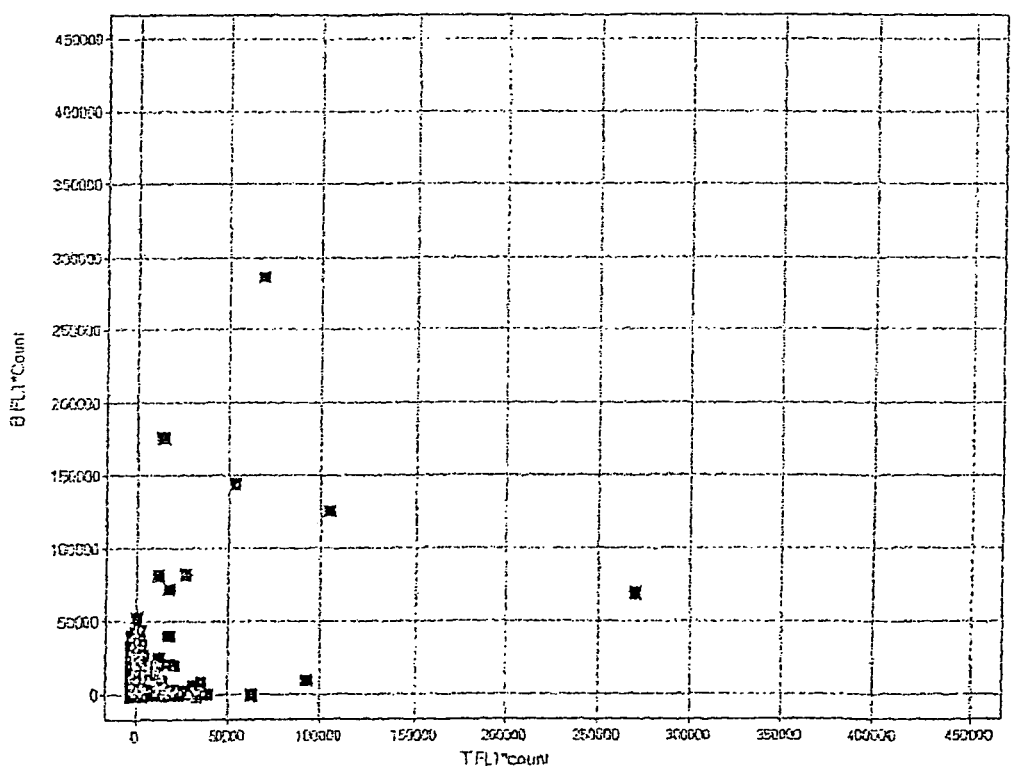

FIG. 8—B cell (Ramos) versus T cell (Jurkat) reactivity of scFv clones: (FIG. 8A) Hit rate of clones selected following three rounds of competition bio-panning utilising the invention (FIG. 8B) Hit rate of clones selected following three rounds of conventional negative (T cell) pre-selection and following positive (B cell) selection. Y axis=B cell reactivity of clones (counts*fluorescence intensity). X axis=T cell, reactivity of clones (counts*fluorescence intensity). ScFv binding was examined using an FMAT macro-confocal high throughput screening instrument.

EXAMPLE 1

Deriving Equations

Applying the Universal Law of Mass Action (LMA), the number of ligands needed to isolate anti-ligands to low expression ligands and/or differentially expressed ligands from display libraries of high diversity may be calculated.

The LMA states that the non-covalent (hydrogen bonding, electrostatic, Van der Waals or hydrophobic forces), reversible binding between an anti-ligand A and its target ligand T, and their complex AT is given by the equilibrium interaction A+T⇔AT with the equilibrium dissociation constant or affinity $K_d=[A][T]/[AT]$.

The equilibrium interaction between anti-ligands with identical specificity (A) for a target ligand (T) may be described as Bound $A(bA)$ ⇔ free $A(fA)$ + free $T(fT)$ with $$Kd = [fA] \times \frac{[fT]}{[bA]} \quad (I)$$

It is known that the total A or T is the sum of free and bound A or T i.e. [A](Total A)=[fA]+[bA], and [T](Total T)=[fT]+[bA]

Therefore in (1) replacing [fA] by [A]−[bA], and [fT] by [T]−[bA]

$$K_d = ([A]-[bA]) \times \frac{[T]-[bA]}{[bA]} \quad (II)$$

Which is rearranged to form $(K_d \times [bA]) = ([A][T]-[A][bA])-([T][bA]-[bA]^2)$ $0 = [bA]^2 - ([A]+[T]+K_d)[bA]+[A][T]$ This simultaneous equation has the solution $$[bA] = \frac{([A]+[T]+K_d)}{2} \pm \sqrt{\frac{([A]+[T]+K_d)^2}{4} - [A][T]}$$

where the negative root is the relevant one:

$$[bA] = \frac{([A]+[T]+K_d)}{2} - \sqrt{\frac{([A]+[T]+K_d)^2}{4} - [A][T]}$$

Substituting concentrations for particle numbers/the number of particles per mole (C)/unit of volume (V) yields $$\frac{bA}{(C \times V)} = \frac{\left(\frac{A}{(C \times V)} + \frac{T}{(C \times V)} + K_d\right)}{2} - \sqrt{\frac{\left(\frac{A}{(C \times V)} + \frac{T}{(C \times V)} + K_d\right)^2}{4} - \frac{AT}{(C \times V)^2}}$$

and simplified to $$bA = \frac{(A+T+(K_d) \times (C \times V))}{2} - \sqrt{\frac{(A+T+(K_d) \times (C \times V))^2}{4} - AT} \quad (III)$$

where
A=total number of anti-ligands A
T=total number of ligands T
V=the reaction volume (litres)
C=Avogadro's constant ($6.022 \times 10^{23}$ particles/mole)

Given that the LMA applies to each reaction between different anti-ligands with given affinity and specificity for their respective target ligands, the number of anti-ligands bound to ligands following a selection process may be calculated by applying the LMA and equation (III).

Furthermore, if there is no qualitative difference between the anti-ligands associated with the populations of subtractor or target ligands, i.e. that there is no change in the physico-chemical properties of the ligand during the method, then the number of anti-ligands that have bound to target ligands at equilibrium will be equal to the total number of bound anti-ligands multiplied by the ratio of target ligands on target ligand constructs to total ligand (subtractor and target ligand):
Introducing
$C_p$=the number of target ligand constructs
$C_s$=the number of subtractor ligand constructs $T_P$=the number of T ligands on $C_p$
$T_S$=the number of T ligands on $C_s$
If target and subtractor constructs are mixed then the total number of ligands will be:

$$T_{Tot}=(T_P \times C_P + T_S \times C_S)$$

And the number of anti-ligands (A) bound to the positive constructs at equilibrium ($bA_P$) is given by:

$$bA_P = bA \times \frac{(T_P \times C_P)}{T_{Tot}} \quad (IV)$$

Furthermore the combination of equations (III) and (IV) yields $$bA_P = \left\{ \frac{(A+T+(K_d) \times (C \times V))}{2} - \sqrt{\frac{(A+T+(K_d) \times (C \times V))^2}{4} - A \times T} \right\} \times \left\{ \frac{(T_p \times C_p)}{((T_p \times C_p)+(T_s \times C_s))} \right\} \quad (V)$$

EXAMPLE 2

Optimising Ligand Concentrations

The equations exemplified in example 1 show that utilisation of high concentrations of both the first subtractor ligand and the second target ligand is instrumental in the efficient retrieval of anti-ligands with specificity for low expression and differentially expressed ligands, as well as for the reduction of anti-ligands with specificity for commonly expressed ligands.

Ligand concentration may be increased by several means. In all cases ligand concentration is increased by moving from two-dimensional coupling of ligand (coupling to a two-dimensional solid-phase) to use of ligand free in suspension or solution (three-dimensional).

In cases where binding is dependent on the ligand being used in its native configuration, such as for cell surface ligands, then ligand concentration is maximised by increasing the ratio of ligand construct surface area to ligand construct volume.

For example, cell surface antigens may be used in the form of small plasma membrane vesicles free in suspension, as opposed to using whole cells fixed to a 2-dimensional surface. This has the additional advantage of increasing the stability of the ligand in suspension or solution, thus promoting the ligand-anti-ligand equilibrium interaction.

If the ligand source has a spherical (or substantially spherical) form, this is described mathematically by the following equation:

$$Ap/Vp=(4\pi r^2)/(4\pi r^3/3)=\pi/3r$$

Where
 Ap=sphere area
 Vp=sphere volume
i.e. the smaller the radius of the sphere, the greater the ratio of ligands/volume and the more particulate (suspension like) the ligand.

EXAMPLE 3

Testing Equation III

Highly diversified molecular libraries, such as phage display libraries, typically comprise some $1 \times 10^{10}$ genotype unique library members. When considering a phage library, a typical 2.5 ml library stock (Volume—V) contains some $2 \times 10^{13}$ total displayed proteins, meaning that each individual library member has 2000 displayed proteins, i.e. that each genotype is represented by 2000 copies. On average, some 10% of these particles (200) (A—target specific anti-ligands) may be estimated to display ligand binding ability.

Insertion of these parameters into equation III and using a desired binding affinity of a good anti-ligand ($K_d \leq 10$ nM) the minimum number of ligands (T) needed to "capture" (bA—bound anti-ligands) a given number of genotype specific anti-ligands may be calculated applying equation III (FIG. 1).

When cells are used as the ligand source, these parameters border that of what is practically feasible using whole cells in conventional biopanning procedures. The number of cells that may be suspended in a 2 ml volume is finite, as increasing cell numbers results in an increased viscosity of the medium, shear forces and impairment of the equilibrium affinity interaction between anti-ligand and target ligand. Overcoming these problems by the methods of the invention permits isolation of anti-ligands to low expression ligands present on only a minority of cells within a heterogeneous cell population.

When attempting to isolate anti-ligands that are specific for ligand(s) that are more abundant in one ligand population compared to another—e.g. antigens on cancer versus non-cancerous cells—there is a still greater demand on utilisation of high concentrations of antigen in a controlled manner. In a highly diversified molecular library there will, in principle, exist anti-ligands to every ligand present in the mixture. Anti-ligands specific for upregulated or unique ligands require enriching relative to common anti-ligands.

Enrichment may be achieved by a competitive biopanning procedure in which ligands from the control population are added in excess.

A molecular library contains anti-ligands with specificity to a large number of different ligands whose concentrations differ between two given complex ligand mixtures—here exemplified by, but not restricted to, cells—as shown in Table I.

It is further assumed that upregulated or unique ligands are rare in comparison to ligands that are similarly distributed between the subtractor and target ligand cell constructs (indicated in Table I by 100 thousand-fold greater anti-ligand representatives for ligand categories TN1 and TN2).

In Table I, antigens (ligand) are divided into categories based on their absolute and relative expression between target and subtractor ligand constructs. In this example, the ligand constructs are cells, and it is assumed that halo different cell populations differ in their expression of certain antigens, but also share expression of certain other antigens.

Antigens belonging to categories TR1 and TR2 are only expressed on target cells (TR=Target cell Restricted); antigen of the TE1, TE2, TE3, and TE4 categories are expressed and enriched at different level on the target cells when compared to the subtractor cells; and target antigens belonging to categories TN1.X and TN2.X are those antigens expressed at equal densities on both the target and subtractor cells, but at different absolute numbers per cell.

Furthermore, it is assumed that antigens expressed at equal densities on target and subtractor cells (TN1.X and TN2.X)

are 100 thousand-fold more common than either the target cell enriched (TE) or unique (TR) antigens.

TABLE I

Anti-ligand molecule categories by positive cell antigen and subtractor cell antigen prevalence

| Anti-ligand Category | Anti-ligand Specificity | Positive cell expression (antigens/cell) $T_p$ | Subtractor cell expression (antigens/cell) $T_s$ |
|---|---|---|---|
| R1 ■ | Antigen TR1 | 1,000,000 | 0 |
| R2 □ | Antigen TR2 | 100,000 | 0 |
| E1 ■ | Antigen TE1 | 50,000 | 1,000 |
| E2 ■ | Antigen TE2 | 50,000 | 10,000 |
| E3 □ | Antigen TE3 | 10,000 | 1,000 |
| E4 ■ | Antigen TE4 | 5,000 | 1,000 |
| N1.1–N1.100000 □ | Antigen TN1.1–TN1.100000 | 100,000 (×100,000) | 100,000 (×100,000) |
| N2.1–N2.100000 ■ | Antigen TN2.1–TN2.100000 | 1,000,000 (×100,000) | 1,000,000 (×100,000) |

EXAMPLE 4

Testing Equation V

If anti-ligands R1, R2, N1 and N2 derived from a highly diversified molecular library are mixed with their respective target antigens TR1, TR2, TN1 and TN2, and where differential expression on target and subtractor cells occurs, then the number of anti-ligands bound to positive cells at equilibrium are given by $$bR1p = \left\{ \frac{(R1 + TR1 + (K_d) \times (C \times V))}{2} - \sqrt{\frac{(R1 + TR1 + (K_d) \times (C \times V))^2}{4} - R1 \times TR1} \right\} \times \left\{ \frac{(TR1_p \times C_p)}{((TR1_p \times C_p) + (TR1_s \times C_s))} \right\}$$

$$bN1p = \left\{ \frac{(N1 + TN1 + (K_d) \times (C \times V))}{2} - \sqrt{\frac{(N1 + TN1 + (K_d) \times (C \times V))^2}{4} - N1 \times TN1} \right\} \times \left\{ \frac{(TN1_p \times C_p)}{((TN1_p \times C_p) + (TN1_s \times C_s))} \right\}$$

and so forth.

Substituting antigen numbers TR1, TR2, TE1, . . . , TE4, TN1 and TN2 with the numbers shown in Table I, and keeping all other parameters constant and as described above, the number of anti-ligands specific for different antigen categories that are bound to target cell (population) antigen at equilibrium, following competitive selection, may be calculated as a function of added target cells and subtractor cells (FIG. 2).

In essence FIG. 2 demonstrates the following:

Increasing addition of target ligand results in the isolation of increasing numbers of anti-ligands with specificity for:

a) Target cell upregulated ligands and target cell unique ligands; and b) Lower abundant target cell upregulated ligands.

Increasing addition of subtractor cells results in better subtraction (removal) of anti-ligands with specificity to ligands expressed at equal densities on target cells and subtractor cells, such that, at high enough ligand concentrations and ratios between target and subtractor cells, all anti-ligands with specificity to commonly expressed ligands will be bound to the subtractor cells (e.g. FIG. 2—$5 \times 10^7$ target cells and $1 \times 10^{10}$ subtractor cells).

In the above example, and given the reaction parameters of FIG. 2, in order for anti-ligands with specificity for all target cell upregulated ligand (including the low expression and low upregulated antigen category E4) to be isolated, $5 \times 10^7$ positive cells need to be utilised in the selection process.

A subtractor ligand excess of two-hundred-fold ($1 \times 10^{10}$) will deplete all anti-ligand with specificity for commonly expressed ligands while anti-ligands with specificity for all target cell upregulated or unique ligands are retained.

In a different selection process set up, where the anti-ligand copy number is not kept constant, utilisation of 5000 copies of anti-ligand (of identical or different genotype) against each ligand would require $1 \times 10^6$ target cells and $5 \times 10^9$ subtractor cells in order to capture anti-ligands of all desirable specificities and the removal of anti-ligands with specificity for all commonly expressed ligands.

For depletion of anti-ligands with specificity for commonly expressed ligands, the ratio of target to subtractor ligand construct used in the selection process needs to exceed the total number of bound anti-ligands with specificity for the highest commonly expressed ligands.

The threshold for such depletion may be determined empirically by titrating the library member input (from a highly diversified molecular library) for the selection process. If the above criteria are met, only anti-ligands with specificity for target cell enriched or target cell unique ligands, will predominate over anti-ligands with specificity for commonly expressed ligands regardless of their affinities (FIG. 3).

Low affinity anti-ligands (Kd=1 μM in FIG. 3) that stick to the cells are then able to be washed away. Due to viscosity effects, increased shearing forces, and impairment of the equilibrium reaction between ligand and anti-ligand, the number of cells needed to fulfil these criteria exceeds that of what is feasible using whole cells, currently available molecular libraries and established biopanning techniques.

As an alternative to immediate depletion of all anti-ligands with specificity for target population/subtractor population commonly expressed ligands, multiple rounds of selection may be performed to enrich for anti-ligands with specificity for ligands uniquely present or upregulated on the target cell. Depending on the quality of the anti-ligand library, the expected abundance of the targeted ligand of interest, and the availability of subtractor ligand construct, such methodology may prove useful.

The ratios between anti-ligands with different specificity increase exponentially with the number of selection rounds. If the total concentration of target ligand (A) is much greater than the concentration of free anti-ligand molecules (fT) ([A]>>>[fT]), as is the case in any given selection process utilising highly diverse molecular libraries, then the concentration of free ligand can be replaced by the total concentration of ligand ([fT]≈[T]) yielding Kd≈[fA]×[T]/[bA]. Replacing [fA] by [A]−[bA] yields Kd≈([A]−[bA])×[T]/[bA] and rearranged to [bA]≈[A]×[T]/(Kd+[T]).

Replacing concentrations for particle numbers/number of particles per mole (C)/volume (V), the number of captured anti-ligands is obtained as bA≈A×T/(C×V×Kd+T).

If target cells are mixed with subtractor cells, the number of anti-ligands captured on target cells ($bA_P$) is given by $bA_P \approx bA \times (T_P \times C_P)/T_{Tot} \approx A \times T_{Tot}/(C \times V \times Kd + T_{Tot}) \times (T_P \times C_P)/T_{Tot} \approx A/(C \times V \times Kd + T_{Tot}) \times (T_P \times C_P)$.

$$bA_p \approx \left( \frac{A \times T_{Tot}}{C \times V \times (K_d + T_{Tot})} \right) \times \left( \frac{T_p \times C_p}{(T_p \times C^p) + (T_s \times C_s)} \right) \quad \text{VI}$$

If:

$$\left( \frac{T_{Tot}}{C \times V \times (K_d + T_{Tot})} \right) \times \left( \frac{T_p \times C_p}{(T_p \times C^p) + (T_s \times C_s)} \right)$$

is constant between selection rounds (reaction parameters other than anti-ligand input ($A_{in}$)) and equal to α for anti-ligand$_A$-ligand$_A$ interaction and β for anti-ligand$_B$-ligand$_B$ interaction, then the number of captured anti-ligands in selection 1 specific for ligand$_A$ is given by $a1 = A_{in} \times \alpha$, and captured anti-ligands specific for ligand$_B$ is given by $b1 = B_{in} \times \beta$.

Similarly, following x-fold amplification of eluted anti-ligand the number of anti-ligands captured on target cell ligands A or B in selection round 2 is given by $a2 = x^*a1 = x^*A_{in} \times \alpha \times \alpha$ (and $b2 = x^*b1 = x^*B_{in} \times \beta \times \beta$.

In selection round 1 the ratio of captured anti-ligands specific for ligand$_A$ to captured anti-ligands specific for ligand$_B$ is given by $(A_{in} \times \alpha)/(B_{in} \times \beta)$. In selection two the ratio will be $(A_{in} \times \alpha \times \alpha)/(B_{in} \times \beta \times \beta)$, and after n selections the ratio will be $(A_{in}/B_{in}) \times (\alpha/\beta)^n$.

Hence, with increasing rounds of panning, anti-ligands with specificity for the target cell unique or upregulated ligand(s) will prevail over anti-ligands with specificity to commonly expressed ligands.

However, multiple panning rounds also decrease the frequency of anti-ligands on the target ligand constructs with specificity for low expression target cell unique or enriched ligands (in comparison to anti-ligands with specificity for highly expressed target cell unique or enriched ligands) e.g. ratios of anti-ligands from categories E4 to R1 increase from 1:44 to 1:25000 after 3 rounds of panning when $10^8$ target cells and $10^9$ subtractor cells are utilised (FIG. 4). This makes the screening process for such anti-ligands extensive, and thereby further demonstrating the need for utilisation of ligand concentrations as high as possible in the selection process.

Multiple selection rounds are performed using reaction parameters other than anti-ligand input (volume, number of target cells and subtractor cells) that are kept constant (FIG. 4).

If large enough concentrations of ligand are utilised all anti-ligands possessing, e.g., nanomolar levels of binding affinity will be bound to their respective ligand. With reaction parameters as used in the previous examples it would take some $7 \times 10^{15}$ ligands to achieve this.

If the lowest abundant ligand population of interest is present at such levels, and if the subtractor ligand population is added at an excess compared to the target ligand population exceeding the number of anti-ligands complexed at equilibrium (200 in this case), anti-ligands specific for ligands that are more abundant in the original target cell population compared to the subtractor cell population will be isolated in numbers increasing in line with the increase in target cell population compared to the subtractor population in a target ligand population abundance independent manner.

Anti-ligands with specificity for ligands found at identical numbers in original target and subtractor ligand populations will be bound to subtractor ligand (Table II/FIG. 5).

TABLE II

| Anti-ligand molecule categories by positive antigen population and negative antigen population prevalence | | | |
|---|---|---|---|
| Anti-ligand Category | Anti-ligand Specificity | Positive antigen population abundance (molecules × $3.5 \times 10^{-14}$) $T_p$ | Negative antigen population abundance (molecules × $3.5 \times 10^{-14}$) $T_s$ |
| ■ | Positive population restricted antigen | 1.00E+06 | 0.00E+00 |
| A ■ | Positive population enriched antigen | 1.00E+06 | 1.00E+04 |
| B ■ | Positive population enriched antigen | 1.00E+05 | 1.00E+03 |
| C ☐ | Positive population enriched antigen | 1.00E+06 | 1.00E+05 |
| D ■ | Positive population enriched antigen | 1.00E+05 | 1.00E+04 |
| E ■ | Positive population enriched antigen | 5.00E+00 | 1.00E+00 |
| ☐ | Positive and negative population commonly abundant antigens (highly abundant) | 1.00E+06 | 1.00E+06 |
| ■ | Positive and negative population commonly abundant antigens (rare) | 1.00E+02 | 1.00E+02 |

EXAMPLE 5

Preferred Embodiment

In a preferred aspect the invention is used to isolate anti-ligands with specificity for cell surface antigens in their native configuration and independent of their nature (protein, carbohydrate, lipid, complex). Additionally the antigens being bound are those upregulated or uniquely expressed on one cell type compared to another (e.g. transformed cancer cell, viral/microbial/parasite/fungal infected cell or other agonist stimulated or infection activated cell versus control cells). (FIGS. 2, 4 and 5)

When utilised for selection of antibody derived anti-ligands (e.g. scFv-, Fab-, or Fv-encoding anti-ligands), the method, simultaneously with the screening process, generates therapeutic antibody candidates that react with target antigen in its native configuration at the cell membrane.

Because such large concentrations of antigen are needed, antigen is used in a form that does not impair the equilibrium reaction. Therefore, antigen is used in forms that occupy minimal space and impose little increase in viscosity and shearing forces.

For example, when anti-ligands to cell surface antigens are sought, a competition biopanning process utilising target whole cells and excess subtractor cell membranes mixed with members of a highly diversified molecular anti-ligand library may be used, followed by density separation on a Ficoll or Percoll/bovine serum albumin gradient and selective isolation of target cells and anti-ligands specific for target cell upregulated and unique antigens.

In this methodology the target ligand (antigen) population is in the form of whole cells (high density) and the subtractor ligand (antigen) is in the form of plasma membrane vesicles or enucleated cells (low density).

The target and subtractor antigen populations are mixed with members of a highly diverse molecular library in a controlled manner based on the equations described herein.

For example, $5 \times 10^7$ target whole cells are mixed with cell membrane vesicles of $1 \times 10^{10}$ subtractor cells and mixed with members from a highly diversified library at an anti-ligand specific copy number of 200 (typically producing anti-ligands of $Kd=10^{-8}M$ when selecting on pure antigen), one can expect to isolate anti-ligands specific for 10-fold or greater upregulated antigens including those expressed at such low densities as 10,000 per target cell.

The reaction is incubated to reach equilibrium. Following competitive biopanning, library members bound to the target population are separated from unbound anti-ligands and those anti-ligands bound to control subtractor antigen by density centrifugation separation, resulting in enrichment of phage specific for highly expressed antigens present among the studied population.

Where the desired target antigen expression is higher in the subtractor population the process is reversed, so that the subtractor ligand population becomes target ligand population and vice versa.

Besides generating anti-ligands with specificity for differentially expressed and unique ligands, use of different density separation means on a density gradient, offers several advantages including:

Physical and spatial separation of anti-ligands complexed to positive ligand from unbound anti-ligands and anti-ligands with specificity for ligand found II the control population.

Ficoll washing increases shear force. Hence, such washing is more efficient and less washing repetitions (panning rounds) are needed; and there is minimal dissociation of specifically bound (higher affinity) anti-ligands of interest.

Does not require tagging or chemical modification of cells (compare FACS (fluorescence activated cell sorter) or MACS (magnetic activated cell sorter) based competitive biopanning) that might alter cell surface ligand configuration/conformation and/or composition.

EXAMPLE 6

All Membrane Vesicles as Separation Means

Whole cells can be replaced by membrane vesicles produced in a higher density media, allowing for even higher concentrations of ligand to be utilized without compromising the equilibrium reaction.

EXAMPLE 7

Testing the Effects of Stimuli on Ligand Up-/Down-Regulations

A further embodiment of the invention may be used to isolate anti-ligands with specificity for cellular ligands that are expressed at a very low density in only a small number of cells within the cell population being studied.

For example, a certain stimulus may be suspected to trigger the upregulation or downregulation of a cell surface antigen present on an unknown cell subpopulation present in blood.

Cells derived from whole blood exposed to this stimulus may be mixed with plasma membranes derived from whole blood prior to exposure to the stimulus, and a competitive biopanning reaction analogous to that described above.

EXAMPLE-8

Diagnostic Use of the Screening Method

A further example of the invention, allows anti-ligands against ligands present at different abundance in biological samples (e.g. plasma, urine, cerebrospinal fluid) to be isolated from highly diversified molecular libraries. Such anti-ligands may subsequently be used for, e.g., protein expression analysis and identification of potential biomarkers.

If sufficiently high concentrations of ligands are used, the method of the invention allows for selective isolation of anti-ligands against up-regulated or unique ligands when comparing protein composition in two different samples (FIG. 2). This ultimately allows for isolation of anti-ligands specific for ligands that are more abundant in one population compared to another population, in a manner that is independent of the relative ligand concentrations within the positive ligand population (FIG. 5).

Due to the extreme concentrations of ligand needed to accomplish the latter, ligand should preferably be used in suspension or solution. For example, target population ligand can be split and tagged at several different positions to minimise destruction and eradication of relevant ligands, while subtractor population ligands can be used untagged or mock treated. Tagging of the positive ligand population provides a means for subsequent retrieval of positive population ligands and binders bound to positive population ligands only by use of tagged ligand complexed with e.g. counter tagged magnetic beads.

An application of tins method would be to pool plasma samples from a population of patients with a certain illness and compare to a plasma samples from a control population. In this case the patient plasma samples would be split and tagged, and the control population would be untagged (see example 11).

EXAMPLE 9

Experimental Testing of Equation(s)

This example demonstrates the experimental use of the preferred embodiment—density competition biopanning using whole cells and cell membrane vesicles to isolate anti-ligands with specificity for a target cell unique ligand.

The model phage pKBitCD40L-2 is a CD40L specific phage and the model phage pBitBLTR-2 is a general mouse fibroblast anti-ligand phage [BioInvent, Sweden].

In order to demonstrate efficient subtraction of phage with specificity for common antigens we used the pBitBLTR-2 phage. This phage was isolated in a previous selection process for its general ability to bind non-transfected, CD32 transfected and CD40L transfected mouse 3T3 fibroblast cells.

FIG. 6 shows the number of kanamycin resistance carrying phage (CD40L specific) and ampicillin resistance carrying phage (mouse fibroblast binder) that were eluted from CD40L transfected 3T3 cells ($5\times10^6$), CD32 transfected 3T3 cells ($2.6\times10^6$), or non-transfected 3T3 cells ($6\times10^6$) following centrifugation based biopanning using a 900 µl phage stock containing $10^6$ pfu CD40L specific phage, $10^6$ pfu mouse fibroblast general binder phage and $10^{10}$ pfu R408 helper phage (no antibiotic resistance).

The affinity of the CD40L specific phage scFv was previously demonstrated to be $K_d=8\times10^{-9}$ M. Mouse fibroblast expression of CD40L and CD32 was confirmed by staining with monoclonal antibodies (MAb) and flow-cytometric analysis (not shown).

CD40L anti-ligand specificity of the kanamycin resistant phage was confirmed by selective retrieval of these phage from CD40L-transfected mouse fibroblasts. The general mouse fibroblast specificity of the ampicillin resistance carrying phage was confirmed by the retrieval of similar members of ampicillin resistance carrying phage following elution from CD40L-transfected, CD32-transfected, and non-transfected mouse fibroblasts (FIG. 7).

The efficacy of utilising excess membrane as subtractors of phage with irrelevant specificity was demonstrated by comparing the ratios of kanamycin and ampicillin resistant phage eluted from
1) a selection process with CD40L-transfected cells only,
2) a pre-selection process utilising whole CD32 transfected mouse fibroblasts at an excess of fourfold; and
3) competition biopanning using a fifty-fold excess of CD32-transfected plasma membranes.

Plasma membrane competition was five-fold more efficient than preselection using whole cells, and utilisation of membranes resulted in a less viscous selection reaction compared to when whole cells were used.

Experimental Methods
Phage Manufacture

An antibody library of human scFv fragments was used to isolate scFv antibody fragments recognising the CD40 ligand antigen (CD40L) on CD40L-transfected mouse 3T3 cells.

In the first pre-selection round the library ($7\times10^{13}$ CFU/mA, 1.8 ml) was incubated with $9.3\times10^6$ un-transfected mouse 3T3 fibroblast cells (1 ml), and 0.2 ml R10 medium {RPMI 1640, 10% FCS, 1×non-essential amino acids, 2 mM EDTA, 50 mM HEPES, (GIBCO BRL, Gaithersburg, Md. 20877, USA)} for 75 min at 15° C. with slow rotation and a total reaction volume of 4.0 ml.

The cells were centrifuged for 10 min at 1500 rpm, 15° C., and the phage containing supernatant transferred to a second pre-selection step analogous to the first, except that CD32-transfected mouse fibroblasts ($1\times10^7$) were used.

Following pre-selection, phage were precipitated by treatment with polyethylene glycol (PEG), resuspended in 1 ml R10 medium, and were used for positive selection on $1\times10^7$ CD40L-transfected 3T3 cells. Positive selection was undertaken at 20° C., during slow rotation, for 3 h.

Cells were washed twice in density gradients consisting of 40% Ficoll/2% BSA/Dulbecco's PBS (Gibco BRL), and once in Dulbecco's PBS only. Bound phage were eluted from cells by re-suspension in 1 ml Glycine/HCl pH 2.2, at room temperature for 15 minutes, followed by neutralisation in 2M Tris-HCl (pH 7.4).

Following centrifugation and collection of eluted phage, the remaining bound phage were eluted in 1 ml 0.4×EDTA-trypsin solution (Gibco BRL) in R10 medium. Pre-selection and positive selection was repeated three times as above.

The specificity of the selected phage scFv was determined by, firstly, screening individual phage clones for reactivity against CD32 transfected or CD40L transfected mouse 3T3 fibroblasts in cell ELISA. Some 20% of these clones showed selective reactivity with CD40L-transfected cells and were picked for further analysis.

The selected clones were converted to scFv format by excision of the gene III fragment and scFv molecules were produced in the nonsuppressor strain *E. coli* HB101. The specificity of the clones was confirmed by scFv whole cell ELISA, and flow-cytometry, using untransfected, CD32-transfected, and CD40L-transfected mouse 3T3 fibroblast cells.

For flow-cytometric analysis scFv binding was detected by biotinylated anti-flag M2 antibody (Sigma Chemical Co, St Louis, Mo., USA) and subsequent Streptavidin-PE (DAKO, Glostrup, Denmark) addition. The affinity of clone 7E for CD40L antigen was Kd=$8\times10$-9M as determined by scatchard blot using whole CD40L-transfected 3T3 cells as all antigenic source (unpublished data).

Selection of the general mouse pBitBLTR-2 phage was carried out essentially as for pKBitCD40L-2, except BLTR-transfected 3T3 cells were used for positive selection. Clone BLTR-2 was selected as a clone that showed equal binding to non-transfected, CD32-transfected, and CD40L-transfected 3T3 cells, as determined by flow-cytometry at the scFv level.

Competitive Bio-Panning
Phage Stock
  $10^6$ cfu of CD40L specific phage (Kan$^r$)
  $10^6$ cfu of mouse fibroblast general binder phage (Amp$^r$)
  $10^{10}$ cfu of R408 helper phage (no antibiotic resistance)
Cells—Positive (Second Target Ligand Construct)
  A1. CD40L transfected mouse 3T3 fibroblasts $5\times10^6$ cells
  C1. $5\times10^6$ CD40L transfected mouse 3T3 fibroblasts only
  C2. $2.5\times10^6$ CD32 transfected mouse 3T3 fibroblasts only (limited)
  C3. $5\times10^6$ cells non-transfected mouse 3T3 fibroblasts only
Cells—Negative (First Subtractor Ligand Construct)
  A1. CD32 transfected mouse 3T3 fibroblast membranes equivalent to $2.5\times10^8$ cells.
Method
  1. A 1 ml phage stock was pre-warmed at 37° C. for 15 min (A 4 ml phagestock was prepared by diluting CD40L specific phage and BLTR general mouse 3T3 cell anti-ligand phage to $10^6$ cfu/ml and R408 helper phage to $10^{10}$ cfu/ml in 2% milk PBS. This phage stock was split to 4×1 ml, transferred to 1.5 ml Eppendorf tubes and was used to perform competitive selections A and B, and conventional pre-selection/selections A and B). The phage stock was vortexed intermittently and centrifuged for 15 min at full speed in an Eppendorf centrifuge, Where a precipitate had formed, the supernatant was transferred to a new Eppendorf tube. Skimmed milk was added to a concentration of 2%.
  2. Naive CD32-transfected 3T3 mouse fibroblast cell plasma membrane preparations were thawed from 5×10 cells on ice. 10 µl was saved for protein concentration determination. Phage stock was re-suspended and mixed with a pipette. The stock was then incubated for 5 min on ice.

3. $5 \times 10^6$ CD40L-transfected 3T3 or non-transfected 3T3 cells were centrifuged at 1300 rpm for 6 min at 4° C.
4. The supernatant was discarded and the CD40L-transfected 3T3 or non-transfected 3T3 cells were re-suspended in the milk-phage-negative cell membrane stock solution from (step 2) and incubated at 10° C. whilst undergoing slow (end-over-end) rotation for 4 hours.
5. The cell/cell membrane/phage incubate was transferred to a 15 ml Falcon tube containing 10 ml 40% Ficoll-Paque Plus and 2% BSA in PBS (with Ca and Mg) and centrifuged at 1500 rpm for 10 min at 4° C.
6. The supernatant was carefully removed by aspirating the uppermost supernatant first (saving the membrane fraction separate (10 µl) for subsequent titration), and then a sequential working down towards the cell pellet containing bound target phage particles. As much supernatant was removed as possible (saving 25 µl supernatant for titration) and the cell pellet resuspended in 500 µl of PBS-2% BSA. The wash performed in (step 5) was repeated once (saving the supernatant for titration).
7. The cells were re-suspended in 1 ml PBS, transferred to a new 15 ml Eppendorf tube and centrifuged at 1260 rpm for 10 min at 4° C. The supernatant was removed using a pipette (saving the supernatant for titration).
8. Phage were eluted from cells by the addition of 150 µl of 76 mM citric acid (pH2.5) in PBS followed by incubation at room temperature for 5 min. The mixture was neutralised by addition of 200 µl of 1M Tris-HCl, pH 7.4. Centrifugation was repeated and the eluted phage saved.
9. The cells were re-suspended in 1 ml trypsin, transferred to a new tube and incubated for 10 min. They were then inactivate with 40 µl 1 mg/ml aprotinin and centrifuged, saving the supernatant for titration. The bacterial pellet was saved for infection of bacteria.

Preselection Biopanning
Phage Stock
$10^6$ cfu of CD40L specific phage (Kan$^r$)
$10^6$ cfu of mouse fibroblast general binder phage (Amp$^r$)
$10^{10}$ cfu of R408 helper phage (no antibiotic resistance)
Cells Positive (Target)—CD40L transfected mouse 3T3 fibroblasts $5 \times 10^6$ cells
Cells Negative (Subtractor)—CD32 transfected mouse 3T3 fibroblasts $2 \times 10^7$ cells
Method
1. A 1 ml phage stock was pre-warmed at 37° C. for 15 min and vortexed intermittently. The phage stock was centrifuged for 15 min at full speed in eppendorf centrifuge. Where a precipitate had formed, supernatant was transferred to new eppendorf tube and skimmed milk added to a concentration of 2%.
2. $2 \times 10^7$ non-transfected 3T3 cells were centrifuged at 1300 rpm, 6 min, 4° C. The supernatant was discarded and the cells re-suspended by the addition of phage stock and by mixing with a 1 ml pipette. This was then incubated at 10° C. undergoing slow (end-over-end) rotation for 4 hours. Then the cells were centrifuged at 1300 rpm for 6 min at 4° C., and the supernatant transferred to a new tube. 20 µl of supernatant was saved for phage titration.
3. $5 \times 10^6$ CD40L-transfected 3T3 cells were detached, washed and centrifuged at 1300 rpm for 6 min at 4° C.
4. The supernatant was discarded, and the CD40L-transfected 3T3 cells re-suspended in the milk-phage stock solution from (step 2). This was then incubated at 10° C. undergoing slow (end-over-end) rotation for 4 hours.
5. The cell/phage incubate was transferred to a 15 ml Falcon tube containing 10 ml 40% Ficoll-Paque Plus and 2% BSA in PBS (with Ca and Mg) and then centrifuged at 1500 rpm for 10 min at 4° C.
6. The supernatant was carefully removed by aspiration of the uppermost supernatant first then sequential removal working down to the cell pellet containing bound target phage particles. As much supernatant as possible was removed (and saved) and the cell pellet re-suspended in 500 µl of PBS-2% BSA. The wash as performed in (step 5) was repeat once (and saved for titration).
7. Cells were re-suspended in 1 ml PBS and transferred to a new 15 ml Eppendorf tube. They were then centrifuged at 1260 rpm for 10 min at 4° C. The supernatant was removed using a pipette (and saved for trituration).
8. Phage were eluted from cells by addition of 150 µl of 76 mM citric acid (pH2.5) in PBS followed by incubation at room temperature for 5 min. The mixture was neutralised by the addition of 200 µl of 1M Tris-HCl, pH 7.4 and then centrifuged and the eluted phage saved.
9. The cells were re-suspended in 1ull trypsin, transferred to a near tube and incubated for 10 min. They were then inactivated with 40 µl 1 mg/ml aprotinin. The cells are centrifuged and the supernatant and pellet saved for infection of bacteria.

Procedure for Phage Amplification from Bacteria (10 ml)
1. Each expression was infected with 10 ml LB (100 µg/ml ampicillin, 15 µg/ml tetracycline with 5 µl from the glycerol stocks)
2. They were grown at 37° C. and 175 rpm until $OD_{600}=0.5$ and $6 \times 10^9$ PFU of R408 helper phage per ml culture added and incubated for 30 minutes at 37° C. and 50 rpm.
3. IPTG solution was added to a final concentration of 1100 M and incubated overnight at 25° C. and 175 rpm.
4. The following day the phage were harvested (as below).

Harvest and PEG Precipitation of Amplified Phage Stocks
1. Bacteria were pelleted by centrifugation for 10 min at 2100 g/(3000 rpm, in Beckman GS-6) at room temperature.
2. The supernatant was sterile filtered through 0.2 µm sterile filter. Any supernatants stemming from the same selection were pooled.
3. Phage were precipitated by adding ¼ volume of phage precipitation buffer (20% PEG 6000, 2.5 M NaCl) and were then incubated for at least 4 hours at 4° C. (Although this can be left incubating for weeks).
4. The preparation was then centrifuged for 30 min at 4° C. and 13000 g.
5. The pellet was completely re-suspended in 500 III PBS, (incubation at 37° C. with agitation for 1 hour) and then stored at 4° C. over night.

Trituration of Phage Pools
1. The phage stock was diluted in sterile PBS. (Suitable dilutions for eluted stocks $10 \times$, $10^2 \times$, $10^3 \times$, $10^4 \times$, and for start stocks or amplified stocks $10^6 \times 10^7 \times$, $10^8 \times$, $10^9 \times$).
2. 100 µl indicator bacteria (grown to $OD_{600}=0.5$) were mixed with 10 µl of each phage dilution and incubated for 30 minutes at 37° C. and 50 rpm.
3. They were then plated on LB agar plates (100 µg/ml ampicillin, 15 µg/ml tetracycline, 1% glucose) and incubated overnight at 37° C.
4. The colonies were then counted and the titre calculated (CFU/ml), (CFU×dilution×100).

Plasma Membranes Preparation from CD32-Transfected Mouse 3T3 Cells

1. Cells were grown to confluency in large (500 cm$^2$) plates. Cells (1×10$^9$) were washed once with versene (50 ml PBS without calcium and magnesium containing 2 mM EDTA), and were then incubated with a small volume of versene (barely covering the cell mat) at 37° C. in a cell incubator.
2. Cells were loosened by hitting the flask against the palm of a hand and then re-suspended in PBS (with Ca and Mg), centrifuged in 50 ml tubes for 7 min at 1200 rpm 4° C., and washed again in PBS (with Ca and Mg).
3. Cells were washed once, re-suspended in approximately 14 ml 0.145 M NaCl and transfected to a 15 ml test tube. They were then centrifuged for 7 min at 1900 rpm, aspirated and re-suspended in 14 ml 0.145 M NaCl. Further centrifugation for 7 min at 1200 rpm was performed and the supernatant removed and the cell pellets frozen at −80° C.
4. The pellet was re-suspended by vortexing in 8 ml (non-transfected) or 4 ml (CD32 cells) of ice-cold Buffer A (10 mM Tris, 1 mM EDTA, 0.25 M sucrose, pH 7.0) freshly mixed with PMSF (phenylmethylsulphonyl fluoride) to a final concentration of 1 mM.
5. The cell suspension was homogenised by 20 strokes of a Dounce homogeniser (type B, pre-cooled) and the homogenate centrifuged in an Eppendorf centrifuge for 10 min at 6000 rpm at 4° C.
6. The supernatant was collected with a Pasteur pipette and the pellet re-suspended in 4 ml (non-transfected) or 2 ml (CD3.2 cells) of Buffer A & PMSF, then homogenised and centrifuged as above. The supernatants were combined and the pellet discarded.
7. The supernatants were layered using a Pasteur pipette, on top of 0.5 ml Cushion Buffer (Buffer C containing 37% of final solution sucrose) and centrifuged for 60 min at 4° C. using rotor SW 60.1 (pre-cooled) at 30,000 rpm (100,000× g). They were balanced carefully for this centrifugation step (to <0.0005 g difference between paired samples).
8. The membrane layer (opalescent) was collected at the cushion interface, where it was tried to get all the material in a small amount of liquid. The collected material was then diluted with 4 vol. of cold Buffer C (10 mM Tris, 1 mM EDTA, pH 7.0) and centrifuged at 30,000 g (rotor JA 25-50, 20,000 rpm) for 30 min at 4° C. The resulting pellet was re-suspended by vortexing in 150 µl of cold Buffer C. The resuspended mixture was frozen and stored at −80° C.
9. Membrane protein concentration was determined by BCA kit (Pierce Biotechnology, Rockford, Ill., USA) to 60 mg/ml.

EXAMPLE 10

Further Experimental Testing of the Equation(s)

This example demonstrates a further experimental use of how the present invention may be used to isolate, from a highly diversified scFv phage library, binders that are specific for cell surface antigens uniquely distributed on one cell population.

The binder hit-rate following three rounds of competitive selection utilising the present invention is shown in comparison to that of a conventional negative pre-selection with a subsequent positive-negative selection (i.e. three rounds of selection).

B lymphocytes express a number of cell surface antigens that are not normally found on T lymphocytes. Such antigens include the B cell immunoglobulin receptor and co-receptors thereof (CD19, CD21), the 4 transmembrane spanning ion channel CD20, and the Fcγ receptor CD32.

B cells, however, express cell surface antigens that are also found common to T lymphocytes, including integrin receptors e.g. LFA-1 (CD11a/CD18), VLA-2, and VLA-4, ICAM-1, complement deactivating receptors e.g. DAF and Protectin, and cytokine receptors like IFN-γR and TNFR. Hence, B and T cells provide an attractive model system to test the applicability of competitive biopanning from a phage scFv display library.

In this experiment 2×10$^3$ phage particles from the highly diversified n-CoDeR library comprising some 10$^{10}$ genotype unique binders are mixed with whole B lymphoma cell line Ramos cells (positive selection), and plasma membrane or crude membrane vesicles from the T leukaemia cell line Jurkat (negative selection). Binders specific for antigens that are uniquely expressed on the B lymphoma cell line Ramos, compared to the T cell leukaemia cell line Jurkat, are to be selectively isolated.

Positive and Negative Cell Number Calculation for Selection

Cell numbers to be used in the different selections round were calculated using equation VI. Reaction parameters used for calculations were as shown in Table III (IIIA & IIIB).

TABLE III

IIIA

| Competition selection | Antigen Expression (Antigens/cell) | |
|---|---|---|
| Phagemid specificity | Positive cell expression | Subtractor cell expression |
| +Cell (B Cell) Restricted Antigen | 1.00E+05 | 0.00E+00 |
| +Cell (B Cell) Enhanced Antigen | 1.00E+05 | 1.00E+03 |
| +Cell (B Cell) Enhanced Antigen | 1.00E+05 | 1.00E+04 |
| +Cell (B Cell) Enhanced Antigen | 5.00E+04 | 1.00E+03 |
| +Cell (B Cell) Enhanced Antigen | 5.00E+04 | 1.00E+04 |
| +Cell (B Cell) Enhanced Antigen | 1.00E+04 | 1.00E+03 |
| (B Cell/T Cell) Commonly expressed antigen (highly expressed) | 1.00E+06 | 1.00E+06 |
| (B Cell/T Cell) Commonly expressed antigen (moderately expressed) | 1.00E+05 | 1.00E+05 |
| −cell (T cell) restricted Antigen | 0 | 1.00E+05 |
| Non-binder | 0 | 0 |
| AF(R1–R2) | | 1.50E+03 |
| AF(R2–R3) | | 6.00E+04 |
| Kd | | 1.00E−08 |
| Avogadro's Constant | | 6.02E+23 |
| Genotype specific phage input R1 | | 2.00E+02 |
| Reaction volume V(L) R1 | | 2.00E−03 |
| Reaction volume V(L) R2 | | 5.00E−04 |
| Reaction volume V(L) R3 | | 5.00E−04 |

| | Number of + cells (B cells) used in selection rounds | −Cell equivalents (T cell membrane vesicles) |
|---|---|---|
| R1 | 5.00E+07 | 2.00E+09 |
| R2 | 5.00E+06 | 1.00E+09 |
| R3 | 5.00E+06 | 1.00E+09 |

IIIB

Phage particles recovered on positive cell

| Phage input | Recovered* | Relative frequency |
|---|---|---|
| R1 | | |
| 2.00E+02 | 59 | 0.296 |
| 2.00E+02 | 53 | 0.264 |
| 2.00E+02 | 27 | 0.133 |
| 2.00E+02 | 30 | 0.152 |
| 2.00E+02 | 14 | 0.073 |
| 2.00E+02 | 7 | 0.035 |
| 2.00E+02 | 5 | 0.024 |
| 2.00E+02 | 5 | 0.023 |

TABLE III-continued

| | | |
|---|---|---|
| 2.00E+02 | 0 | 0.000 |
| 2.00E+02 | 0 | 0.000 |
| R2 | | |
| 9.E+04 | 1.3E+04 | 0.482 |
| 8.E+04 | 8.7E+03 | 0.336 |
| 4.E+04 | 1.5E+03 | 0.953 |
| 5.E+04 | 2.7E+03 | 0.102 |
| 2.E+04 | 4.1E+02 | 0.016 |
| 1.E+04 | 1.3E+02 | 0.005 |
| 7.E+03 | 3.6E+01 | 0.001 |
| 7.E+03 | 3.3E+01 | 0.001 |
| 0.E+00 | 0.0E+01 | 0.000 |
| 0.E+00 | 0.0E+00 | 0.000 |
| R3 | | |
| 8.E+08 | 1.1E+08 | 0.60022 |
| 5.E+08 | 5.8E+07 | 0.32542 |
| 9.E+07 | 3.3E+06 | 0.01855 |
| 2.E+08 | 9.4E+06 | 0.05248 |
| 2.E+07 | 4.6E+05 | 0.00259 |
| 8.E+06 | 9.4E+04 | 0.00053 |
| 2.E+06 | 1.1E+04 | 0.00006 |
| 2.E+06 | 9.7E+03 | 0.00005 |
| 0.E+00 | 0.0E+00 | 0.00000 |
| 0.E+00 | 0.0E+00 | 0.00000 |

Table III Selection reaction parameters used in the whole Cell (Ramos)/membrane vesicle (Jurkat) competitive biopanning. Kd=lowest relevant affinity of target ligand specific anti-ligands to be isolated, genotype specific phage input R1=anti-ligand (phage scFv copy number of starting anti-ligand library), AF=amplification factor used to calculate phage input into selection rounds R2 and R3 following elution and amplification of phage from rounds R1 and R2 respectively. Relative frequency=the expected frequency of isolated anti-ligands with specificity for antigen belonging to one antigen category compared to all anti-ligands isolated.

Positive and negative cell numbers were chosen such that, following three rounds of selection, binders with specificity for antigens expressed uniquely on B cells will be enriched 10,000-fold over an antigen expressed at equal density on B and T cells.

The input number of phage binders specific for different categories of antigen (positive cell enriched, positive cell unique, or positive/negative cell commonly expressed antigen) in selection rounds 2 and 3 was calculated by multiplying the calculated number of eluted phage, specific for different categories of antigen following selection rounds 1 and 2, with the amplification factor (AF).

The amplification factor was obtained by dividing total number of amplified phage following the relevant selection round with the total number of eluted phage from the same selection round.

FIGS. 8A and 8B show the comparison of biopanning by the present method and by previously known methods on B cell (Ramos) versus T cell (Jurkat) scFv clones. The B cell reactivity and specificity of ScFv's isolated using the invention is dramatically enhance compared to that of ScFv selected by conventional biopanning.

Experimental Methods

Cell Cultures

The Jurkat T cell line, clone E6-1, and the Ramos B lymphoma cell line, were obtained from ATCC and cultured in RPMI 1640 supplemented with 10% FCS (heat-inactivated for Ramos Cells only), 10 mM HEPES and 1 mM Sodium pyruvate, in a humidified atmosphere at 37° C. The cells were maintained at $1$-$2\times10^6$ cells/ml ($<1\times10^6$ cells/ml for Jurkat).

Jurkat T Cell Plasma Membrane Preparation

Jurkat T Cell Culture

Jurkat E6-1 cells were maintained in RPMI-1640 with Glutamax I (Gibco, #61870-010) supplemented with 10% foetal calf serum (Gibco, Lot no 1128016) 1 mM Sodium pyruvate (Gibco) and 10 mM Hepes buffer (Gibco) in a humidified atmosphere of 5% $CO$, at 37° C., and at cellular densities between $10^5$ to $1\times10^6$ cells/ml. In the final passage, cells were allowed to reach a maximal density of $2\times10^6$, at which point they were harvested.

Cell Disruption

1. Cells were harvested from culture by centrifugation in 500 ml Centrifuge tubes (Corning, #431123) placed in tube adapters, 1500 rpm, 15 min at 4° C.
2. The supernatant was discarded and washed in 0.145M NaCl. Cell suspensions were pooled, cells counted ($5\times10^9$ cells total), and centrifugation repeated.
3. Cell disruption was performed by hypo-osmotic shock in 1 mM $NaHCO_3$ 1.5 mM MgAc pH 7.4 on ice for 10-300 min and subsequent nitrogen cavitation occurred in a Yeda press, 40 bar (4000 kPa) for 15 min at 0° C. Cell concentration did not exceed $5\times10^7$ cells/ml.
4. Following disruption 150 µl 0.5M EDTA was added to the homogenate suspension to yield a final EDTA concentration of 1 mM (addition of EDTA prevents aggregation of membrane vesicles).
5. A) Crude membrane isolation: The homogenate (50 in) was centrifuged for 10 min at 1900 g (4000 rpm in a SS34 rotor) to remove unbroken cells and nuclei, and the supernatant collected. Washing and re-centrifugation of pellet was avoided, as the fragile nuclei tend to disrupt, causing DNA leakage and aggregation; or B) Plasma membrane isolation: 10 ml of 37.2% sucrose was layered at the bottom of 6×38.5 ml Beckman ultra centrifugation tube, and 6×27 ml of the cell homogenate from step 2 above was carefully layered on top. The tube was centrifuged at 27000 rpm in a swing-out SW28 rotor (6×39 ml nominal capacity) for 2 h 45 min at 4° C. Plasma membranes were isolated from the tubes as the white band of the interphase between the sucrose cushion and the sample phase, and PM were pooled, split between 4×35 ml tubes and diluted in TE buffer (1 mM Tris/0.25M sucrose/0.25M EDTA buffer) to a total volume of 35 ml.
6. Ultra-centrifugation was in a Beckman Type 45.Ti rotor (nominal capacity 6×94 ml Nalgene tubes) at 40.000 rpm (approx. 200.000×g) for 1 h at 4° C.
7. The supernatants were discarded and any remaining buffer was removed using a 1 ml Finnipipette. The plasma membrane pellets were scraped off the bottom of tubes with a metal bar, and transferred to a small dounce homogeniser. Pelleted membranes were re-suspended by homogenisation in a total volume of 2.5 µl TE-buffer containing 10 mM Hepes (10 mM Hepes/1 mM Tris/0.25M sucrose/0.25M EDTA buffer) by 5-10 strokes with a loose fitting Dounce glass piston. Approximately, membranes derived from some $2\times10^9$ Jurkat cells can be resuspended per ml of resuspension (TE) buffer.

Protein Concentration Determination

Protein concentration determination was performed using the BCA kit according to the manufacturer's instructions. Briefly, a double BSA standard was prepared by 2-fold dilutions (10 µl sample+10 µl buffer) in PBS of a 2 mg/ml BSA stock solution. A standard curve was generated and used to determine the total protein concentration of membrane samples.

Plasma Membrane Activity (by Alkaline Phosphatase Assay)
Alkaline Phosphatase Solutions
Substrate Solution:
  1 tablet p-NPP per 10 ml borate buffer (1.5 mg/ml final concentration) in
  50 mM sodium borate buffer (pH 9.8), 1.0 mM $MgCl_2$ Triplicate samples were diluted in Borate/MgCl2 buffer by transferring 50 µl sample to 50 µl dilution buffer (50 mM sodium borate buffer (pH 9.8), 1.0 mM $MgCl_2$). 200 µl substrate solution (1 tablet p-NPP per 10 ml borate buffer to 1.5 mg/ml final concentration in 50 mM sodium borate buffer, pH 9.8, 1.0 mM $MgCl_2$) was added to two of three samples for each dilution. The samples were then incubated at 37° C. for 60 plus minutes. The absorbance of the supernatant was measured at 410 nm, and the values from appropriate control well(s) (e.g. total Nitrogen cavitated cell homogenate, nuclei and heavy mitochondria excluded) where substrate was not added were subtracted. The results were plotted and analysed.

Selection Procedure: Competitive Bio-Panning Protocol
Reaction Parameters
1st Selection Round
  n-CoDeR Lib2000 phage stock comprising $10^{10}$ genotype unique phagemid particles (Amp$^r$) amplified to $2\times10^{13}$ total pfu in 1.6 ml 2% milk-PBS (with Ca and Mg).
Total reaction volume 2.5 ml
Positive—$5\times10^7$ Ramos B cell lymphoma cells
Negative—Jurkat T cell crude membranes derived from $2\times10^9$ cells
$2^{nd}$ Selection Round
  $1.5\times10^{12}$ phage eluted from previous selection round and then amplified, precipitated and re-suspended in 100 µl 2% milk-PBS (with Ca and Mg).
Total reaction volume 0.5 ml
Positive—$5\times10^6$ Ramos B cell lymphoma cells
Negative—Jurkat T cell crude membrane vesicles derived from $1\times10^9$ cells
3rd Selection Round
  $1\times10^{12}$ phage eluted and amplified from previous selection round re-suspended in 100 µl 2% milk-PBS (with Ca and Mg).
Total reaction volume 0.5 ml
Positive—$5\times10^6$ Ramos B cell lymphoma cells
Negative—Jurkat T cell plasma membrane vesicles derived from $1\times10^9$ cells
Method
A 2 ml phage stock was pre-warmed at 37° C. for 15 min and vortexed intermittently. The phage stock was centrifuged for 15 min at full speed in an eppendorf centrifuge. Where a precipitate had formed, the supernatant was transfected to a new eppendorf tube and resuspended in non-fat milk to a final concentration of 2%.

Thaw control Jurkat cell plasma membrane preparations from $2\times10^9$ cells ($1\times10^9$ cells biopanning rounds 2 and 3) on ice. (10 µl was also saved for protein concentration determination.) The thawed plasma membrane preparations were resuspended by adding phage stock and by mixing with a pipette and subsequently incubated for 15 minutes on ice.

$5\times10^8$ is ($5\times10^6$ cells biopanning rounds 2 and 3) Ramos cells were (centrifuged at 1200 rpm, 6 min, 4° C.

The supernatant was discarded and the Ramos cells resuspended in the milk-phage-negative cell membrane stock solution from biopanning round 2 and incubated at 10° C. and subjected to slow (end-over-end) rotation for 4 hours.

The cell/cell membrane/phage incubate was transfected to a 15 ml Falcon tube containing 1 ml 100% (trypan blue stained) Ficoll at the bottom, and 9 ml overlaid 40% Ficoll-Paque Plus in 2% BSA/PBS (with Ca and Mg). Centrifuge at 1500 rpm for 10 min, 4° C. The tube was rotated 180° and centrifuged for a further 1 minute in order to dislodge cells from the tube wall.

The interface containing whole Ramos cells and bound phage was carefully aspirated using a syringe and a higher gauge needle (e.g. Microbalance 3-19GA11/2 1, 1×40 TW PM). The needle is inserted just below the cell-containing interface with the bevelled end of the needle facing up. The cell layer is collected (approximately 150 µl) and the needle pushed through the plastic of the tube opposite to the entrance hole. The contents of the syringe are expelled into a fresh tube, and washed twice by sucking up fresh PBS into the needle (still situated as piercing the tube). The harvest cell suspension was resuspended in 500 µl of PBS-2% BSA and washing repeated, saving the supernatant for titration.

Cells were resuspended in 1 ml PBS and transferred to a new 155 ml Eppendorf tube in which they were centrifuged at 1260 rpm for 10 min, 4° C. The supernatant was removed using a pipette, saving the supernatant for titration.

The phage were eluted from cells by addition of 150 µl of 76 mM citric acid (pH2.5) in PBS followed by incubation at room temperature for 5 min. The mixture was neutralised by addition of 200 µl of 1M Tris-HCl, pH 7.4. The cells were then centrifuged and the eluted phage saved.

The cells were resuspended in 1 ml trypsin and transferred to a new tube and incubated for 10 min before inactivation with 40 µl 1 mg/ml aprotinin. The cells were centrifuged, saving the supernatant for titration.

Control Selection Protocol
  Control selection was performed using conventional negative pre-selection and subsequent positive selection using cell concentrations.
Reaction Parameters
Cells
  In all selection rounds
Total reaction volume 4 ml
Negative pre-selection—$1\times10^8$ Jurkat T cell cells
Positive—$2\times10^7$ Ramos B cell lymphoma cells
$1^{st}$ Selection Round
  n-CoDeR Lib2000 phage stock comprising $10^{10}$ genotype unique phagemid particles (Amp$^r$) amplified to $2\times10^{12}$ total pfu in 2.5 ml 2% milk-PBS (with Ca and Mg)
$2^{nd}$ Selection Round
  $2.6\times10^{10}$ phage eluted from previous selection round and then amplified, precipitated and re-suspended in 2.5 ml 2% milk-PBS (with Ca and Mg)
3rd Selection Round
  $5.4\times10^{10}$ phage eluted and amplified from previous selection round re-suspended in 2.5 ml 2% milk-PBS (with Ca and Mg)
Method
A 2.5 ml phage stock was pre-warmed at 37° C. for 15 min and vortexed intermittently. The phage stock was centrifuged for 15 min at full speed in an eppendorf centrifuge. Where a precipitate has formed, the supernatant was transferred to a new Eppendorf tube and subsequently resuspended in non-fat milk to a final concentration of 2%.

$1\times10^8$ Jurkat T leukaemia cells were centrifuged at 1200 rpm, 6 min, 4° C. and resuspend in 1.5 ml 2% milk-PBS and subsequently by adding phage stock and by mixing with a pipette. They were then incubated for 24 hours at slow rotation, 4° C.

The cell-phage incubation mixture was centrifuged at 300 g for 6 min, 4° C. The supernatant was discarded and washed three times in 15 ml PBS, re-centrifuged and the supernatant collected.

$2\times10^7$ Ramos cells were centrifuged at 300×g, 6 min, 4° C. and resuspended in a collected phage mixture from negative pre-selection and incubated at 4° C. for 4 hours with slow agitation.

The Ramos/phage incubation mixture was centrifuged and the supernatant discarded and the Ramos cells washed three times in 15 ml PBS.

Phage were eluted from cells by addition of 150 µl of 76 mM citric acid (pH2.5) in PBS followed by incubation at room temperature for 5 min. The mixture was neutralised by addition of 200 L of 1M Tris-HCl, pH 7.4. The cells were centrifuged and the eluted phage saved.

The cells were re-suspended in 1 ml trypsin, transferred to a new tube and incubated for 10 min. They were then inactivated with 40 µl mg/ml aprotinin, centrifuged and the supernatant saved for titration.

Amplification on Large Plates Following Selection Rounds 1 and 2

1. 3×10 ml HB101F' tubes were started (one for each selection to be performed+ one for OD600 measurement) 2.5-3 h before use. 50 µl overnight culture to 10 ml LB containing 15 µg/ml tet was used. OD is checked on one culture after approximately 2.5 h
2. The tubes were infected with half the eluted phage at $OD_{600}=0.5$
3. The tubes were incubated for 30 minutes at 37° C. and 50 rpm, and for proper phenotyping an additional 30 rain at 37° C., 200 rpm.
4. The bacteria were concentrated (10 ml) by centrifugation for 10 minutes at 2060×g (3000 rpm Beckman GS-6).
5. They were then resuspended in part of the supernatant (approximately 3 ml) and spread on a large 500 cm² plate (100 µg/ml amp+15 µg/ml tet+1% glu)/selection.
6. The plates were then incubated over night at 30° C.
7. The bacteria were collected from the plates by adding 5 ml of LB (100 µg/ml ampicillin, 15 µg/ml Tetracycline) per plate and the bacteria scraped off. The plate was tilted and the solution aspirated.
8. The plates were washed with an additional 3 ml LB medium as above and pooled with the first bacterial suspension in a 50 ml Falcon tube.
9. The bacteria were concentrated by centrifugation for 10 minutes at 2100×g/3000 rpm, Beckman GS6 at room temperature and resuspended in 1 ml of LB (+100 µg/ml Amp and 15 µg/ml Tet).
10. 500 µl 50% glycerol was added to 1 ml (transferred from a target volume as used in 5) and the glycerol stock frozen at −80° C.
11. 2×10 ml LB+amp (100 µg/ml)+tet (15 µg/ml) was infected with 2.5 µl (5 µl) of the glycerol stock of step 10, and grown until $OD_{600}=0.5$.
12. $6\times10^9$ PFU of R408 helper phage were added per ml culture and incubated for 30 minutes at 37° C. and 50 rpm.
13. IPTG solution was added to a final concentration of 100 µM (i.e. 2 µl from 0.5 M stock per 10 ml culture and incubated overnight at 25° C. (pili formation is inhibited at greater temperature) and 175 rpm.

Harvest and Precipitation of Amplified Phage Stocks

1. Bacteria were pelleted for 10 minutes at room temp. 2100×g (3000 rpm, in Beckman GS-6) and the supernatant sterile filtered through 0.2 µm sterile filter.
b 2. The appropriate tubes were pooled and the phage precipitated by adding ¼ volume of phage precipitation buffer and incubated for at least 4 hours at 4° C. (and can be incubated for weeks).
3. The tubes were then centrifuged for 30 minutes at 4° C. and 13000×g.
4. The pellet was resuspended completely in 100 µl PBS over night at 4° C.

Titration of Phage

Materials: Overnight culture of *E. coli* HB 101F'
v-bottom microtitre plate
1×PBS (sterile)
LB-medium
LA+amp (100 µg/ml)+tet (15 µg/ml)+1% glucose plates 1. 10 ml LB+tet (15 µg/ml) was inoculated with 100 µl of an over-night culture of *E. coli* HB101 F' and incubated at 37° C., 175 rpm, until $OD_{600}=0.5$ (approx. 2-2.5 h).
2. For amplified phage stocks, the phage were diluted $10^5$ times in PBS in a v-bottom microtitre plate before infection. Eluted phage are used undiluted for infection (see below).
3. When the *E. coli* cells reached OD600=0.5, 100 µl of the culture was transferred to every second well of the first column of wells on a v-bottom microtitre plate. The three following wells in the row were filled with 90 µl LB-medium.
4. 10 µl of the phage stocks were transferred (diluted or undiluted as above) to 100 µl bacteria in the microtitre plate and incubated for 30 min at 37° C., 50 rpm.
5. The infected bacteria were diluted by sequentially transferring 10 µl from each well to the next well filled with 90 µl LB.
8. 10 µl from each well was spotted onto a dry LA+amp+tet+ 1% glu plate using, a multi-channel pipette with every second tip removed, i.e. with only four tips. 4×5 spots were spotted onto on each LA plate and allowed to dry before inverting the plates for incubation at 37° C.
9. The colonies were counted and the titre (CFU/ml) calculated, (CFU×dilution×100).

Trituations Performed

TABLE IV

| | | Dilutions |
|---|---|---|
| After Selection Round 1 | Start pool | $10^7 \times 10^8 \times 10^9 \times 10^{10} \times 10^{11}$ |
| | HB101F' BnonT-C.1 eluate | $10^2 \times 10^3 \times 10^4 \times 10^5 \times 10^6$ |
| After Selection Round 2 | HB101F' BnonT-C.1 amplified | $10^7 \times 10^8 \times 10^9 \times 10^{10} \times 10^{11}$ |
| | HB101F' BnonT-C.2 | $10^5 \times 10^6 \times 10^7 \times 10^8 \times 10^9$ |
| After Selection Round 3 | HB101F' BnonT-C.2 amplified | $10^7 \times 10^8 \times 10^9 \times 10^{10} \times 10^{11}$ |
| | HB101F' BnonT-C.3 | $10^5 \times 10^6 \times 10^7 \times 10^8 \times 10^9$ |

Amplification on plates for glycerol stocks, and over night culture for minipreps (following selection round 3).

Reaction Materials
3×10 ml HB101F' with OD 0.5 are needed (10 ml for each target and 10 ml for titration)
3 large 500 cm² plates are needed (amp+tet+glu).

Method

For each selection:
1. Half of each eluate from selection 3 is used to infect 10 ml log phase bacteria ($OD_{600}$ 0.5) which are then incubated for 30 min. at 37° C., 50 rpm and grown for 30 min at 37° C., 175 rpm. 10 ml in media containing 200 µg/ml Ampicillin is added and divide in 2 parts of 10 ml each.
2. The bacteria were concentrated (10 ml) by centrifugation for 10 minutes at 2100×g/3000 rpm, Beckman GS-6 at room temperature and resuspended in a small volume to be spread on one 500 cm² plate (100 µg/ml amp+15 µg/ml tet+1% glu) and grown over night at 30° C.

3. Miniprep: 10 ml were spun down and resuspended in 6 ml LB containing 0.1% glucose and 100 μg/ml amp and Grow over night at 30° C.
4. The bacteria were collected from the plates by adding 3-5 ml of LB (100 μg/ml ampicillin, 15 μg/ml Tetracycline) per plate and scrape of bacteria. Tilt the plate and aspirate the solution.
5. The bacteria were concentrated by centrifugation for 10 minutes at 2100×g/3000 rpm, Beckman GS6 at room temperature and resuspended in 1 ml of LB (+Amp/Tet as above). Add 500 μl 50% glycerol and the glycerol stock frozen at −80° C.
6. Minipreps were prepared from 3 ml of culture according to protocol from the kit manufacturer (BioRad).

Conversion to scFv Format after Selection 3

The pMil vector was digested with EagI, an enzyme that cuts on both sides of gene III. The vector was then re-ligated followed by a killer cut using EcoRI. This enzyme has a site in gene III and thus will destroy non-converted vectors.

A digestion mix was prepared using.
Phagemid 6.25 μl (0.21-0.66 μg)
NEBuffer 3 0.75 μl
EagI (10 U/μl) 0.5 μl
MQ-H$_2$O Added to 7.5 μl and incubated at 37° C. for 2 h with heat inactivation for 20 min at 65° C.

Ligation of the vector is performed with
EagI digested phagemid 3 μl
MQ-H$_2$O 20 μl
Incubated for 5 min at 45° C. and put on ice.
5× ligase buffer 6 μl
T4 DNA ligase (1 U/μl) 1 μl
    30 μl Incubated for 2 hours at room temperature and heat inactivated at 65° C. for 10 minutes.

The killer cut is performed with

| | |
|---|---|
| Ligated material | 30 μl |
| 10x REACT ® 3 | 3.6 μl |
| EcoRI (10 U/μl) | 2 μl |
| 1 M NaCl | 0.4 μl |
| MQ-H$_2$O | 4 μl |
| 40 μl | incubated for 90 min at 37° C. and heat inactivated for 10 minutes at 65° C. |

The ligate is stored at 4° until used.

Transformation

The ligate produced above was transformed into *E. coli* TOP10, see table below.

One tube (100 μl/tube) of chemically competent TOP10 cells were thawed and incubated on ice for 10 min. 10 ng ligate were added per tube (3.2 μl ligates made above) and incubate on ice for 30 min.

The tubes were then incubated at 42° C. (water bath) for 90 s, and further incubated on ice for 1-2 min.

900 μl LB was added to each tube and incubated at 37° C., 1 h, 200 rpm.

The content of each tube was spread on one large LA-Amp (100 μg/ml)-Glu (1%) plate, and incubated overnight at 37° C.

Colony Picking

A total of 960 clones were picked from each of the two selections from the large LB plates to 10×96 well microtitre plates using a Genetix "Q-bot" colony picking system.
1) LB media was mixed with appropriate antibiotics and glucose 1% and Greiner Flat 96 well 655501 plates filled with media, 150 μl/well.
2) Colonies were picked with the Q-Bot according to the protocol, and the plates incubated at 37° C. over night without shaking.

Expression of Clones in 96 Well Format
1) The expression plate (Greiner Round 96 well 650101) was filled with media 100 μl/well including appropriate antibiotics and inoculated with 5 μl/well from the master plate and the expression plate incubated at 37° C., 600 rpm for 3.5 h.
2) The production of scFv was induce with 25 μl/well of media including appropriate antibiotics and 2.5 mM IPTG.
3) The expression plate was incubated for 10 h at 37° C., 600 rpm.
4) 80 μl of IM PBS was added to the filter plate and filter added to the stock plate.
5) 80 μl was transferred from the expression plate to the filter plate and filter to the stock plate. The Stock plate was stored at +4° C.

Screening of Clones in 96 Well Format

Clones were screened in a macro confocal FMAT 8100 HTS system (Applied Biosciences, Foster City, Calif., USA). Gates were set using B and T cell specific monoclonal antibodies (anti-CD19 and anti-CD3 respectively) so that B cell positive signal was obtained only by staining with anti-CD19 primary antibody, and T cell positive signal only with anti-CD3 primary antibody. (FL1<10666, FL2<2026, Colour: 0.17-0.425, Size 10.0-66.66).

Materials:
αCD45 0.5 mg/ml (BD Biosciences cat no 555480)
αCD19 0.5 mg/ml (BD Biosciences cat no 555410)
αCD3 0.5 mg/ml (BD Biosciences cat no 555330)
Purified clone 31 0.154 mg/ml 010515 KMN
α-HIS (R&D Systems MAB050, 8.43 mg/ml)
αmouse-Cy5 (Amersham Bioscience PA45002)
PBS (Gibco, Cat no 14040-091)
Hepes Buffer (Gibco, Cat no 15630-056)
Buffer: PBS+10% Hepes buffer
Cell media: RPMI 1640 with 10% FCS, 10 mM Hepes, 1 mM Sodium
Pyruvate
LB media
Method
1) 10,000 cells/well diluted in cell media, were added to 40 μl well incubate grow on at 37° C., 5% CO$_2$.
2) 10 μl/well of scFv were added to one plate with B cells and one plate with T cells. Also added were α-CD45 to column 2, α-CD19 to column 3 and α-CD3 to column 4, and the plates incubated for 1 hour.
3) α-mouse-Cy5 diluted in buffer were added, 20 μL/well (dilution 1:1000, final dilution, working dilution 1:286) to the control plates. αmouse cy5+αHis diluted in buffer (dilution 1:1000 and 1:5000 final dilution, 1:286 and 1:1429 working dilution) were also added.
4) The plates were read on the FMAT 8100 HTS systems after 4 h. The reading repeated after an over night incubation.

EXAMPLE 11

Pharmaceutical Compositions

A further example of the invention provides a pharmaceutical composition comprising an anti-ligand (the active ingredient) isolated according to the method of the invention.

The aforementioned compounds of the invention or a formulation thereof may be administered by any conventional method including oral and parenteral (e.g. subcutaneous or intramuscular) injection. The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free.

EXAMPLE 12

Screening without Cell Culture

The present invention allows for biomarker and target discovery directly at the protein level by use of e.g. highly diversified molecular libraries. The present prophetic example demonstrates its applicability, for selective isolation of binders with specificity to antigens upregulated or unique in one plasma sample (e.g. from a cancer patient) compared to another (from a healthy control).

A highly diversified molecular library containing $10^{11}$ genotype unique members at a binder copy number of approximately twenty (effective number of binders displaying binding ability, non-displaying examples are removed by means of affinity purification) is precipitated by polyethyleneglycol treatment and re-suspension in 20 µl 10% milk-PBS solution. Isolated binders from selection using this library have nanomolar affinity (Kd=$1\times10^{-9}$) for the relevant antigen.

Whole plasma (albumin and some other high abundance large protein that are not suspected to differ between the two patients are removed by size exclusion chromatography) from a cancer patient and a healthy control rue collected and treated as follows:

The cancer patient plasma sample is split and biotinylated at three different amino acid positions, in order to minimise the loss of relevant antigen epitopes being destructed by the chemical biotinylation process.

The control plasma is subjected to a mock treatment (treatment without addition of biotin). Control plasma is then concentrated forty times by appropriate treatment, and is subsequently mixed with the plasma sample from the cancer patient in equal volumes (total volume=11.0 ml).

The mixture produced is mixed with the blocked molecular library above, and the produced plasma/binder mixture is incubated over night at 4° C. at slow end-over-end rotation.

Following selection biopanning, capture beads e.g. streptavidin coated magnetic particles (streptavidin coated µMACS from Miltenyi, USA; bead diameter=50 nm) are added and used to isolate biotinylated proteins from the cancer patient plasma sample and antigen bound molecular library binders (Siegel et al., 1997).

The magnetic beads are added at a molar ratio sufficient to capture all biotinylated antigen added (equivalent of total cancer patient biotinylated plasma protein concentration).

The mixture is transferred to a magnetic separation column pre-treated as described by Siegel, L. et al., J Immunol Methods, 206(1997), pp73-85:

1. Before addition of selection suspension, the MACS column is loaded with 2% BSA-PBA (BPBS) to fill the lower part (that will later be outside the magnetic field), and so that subsequently added selection mix will distribute evenly through the "magnetic" part of the column without clogging. A 30—gauge×½ inch needle is mounted at the column is outlet port to restrict the flow rate to 10 l/min.
2. Once loaded, the column is placed inside the magnet for 2 min.
3. A total of 3 washes with BPBS are performed for each selection round, the first of which is performed with the needle attached to the column outlet port, and subsequent washings performed without a flow-restricting needle (flow-rate ~200 µl/min).
4. Following the last wash, the column is removed from the magnet and the bead-coated/phage coated/biotinylated antigen are flushed off the column with 500 µl PBS using the plunger from a 5-cc syringe (Beckton-Dickinson, Franklin Lakes, N.J., USA).
5. Elution is achieved by acid, base or otherwise suitable means (e.g. enzymatic cleavage if the molecular library members contain a specific enzyme cleavage site)
6. The beads are centrifuged, and eluted binders are saved and titrated.

Using the above experimental set-up, one may expect to isolate binders with specificity for antigens 10-fold or more upregulated (or uniquely present) in the patient plasma sample compared to the control plasma sample and present at sub-nanomolar levels (or greater) in the cancer patient sample, whilst eliminating binders with specificity for antigens present at equal abundance in the original cancer patient ant control patient samples.

Table V shows expected relative numbers (theoretical, assuming no dissociation of nanomolar binders during washing) of binders with specificity for different categories of antigen.

TABLE V

| Binder Category | Cancer patient plasma antigen concentration (moles/litre) | Healthy control plasma antigen concentration (moles/litre) | Kd = 1 × 10$^{-9}$ M antigen specific binder copy number input | Binders isolated following biopanning |
|---|---|---|---|---|
| Positive cell restricted antigen | 3.3 × 10$^{-8}$ | 0.00E+00 | 2.00E+0 | 19 |
| Positive cell enriched antigen | 3.3 × 10$^{-8}$ | 3.3 × 10$^{-9}$ | 2.00E+01 | 4 |
| Positive cell enriched antigen | 3.3 × 10$^{-8}$ | 3.3 × 10$^{-10}$ | 2.00E+01 | 14 |
| Positive cell enriched antigen | 3.3 × 10$^{-9}$ | 3.3 × 10$^{-10}$ | 2.00E+01 | 4 |
| Positive cell enriched antigen | 3.3 × 10$^{-10}$ | 3.3 × 10$^{-11}$ | 2.00E+01 | 2 |
| Positive cell enriched antigen | 1 × 10$^{-10}$ | 0 | 2.00E+01 | 1 |
| Common antigen (highly expressed) | 3.3 × 10$^{-6}$ | 3.3 × 10$^{-6}$ | 2.00E+01 | 0 |

TABLE V-continued

| Binder Category | Cancer patient plasma antigen concentration (moles/litre) | Healthy control plasma antigen concentration (moles/litre) | $Kd = 1 \times 10^{-9}$ M antigen specific binder copy number input | Binders isolated following biopanning |
|---|---|---|---|---|
| Common antigen (moderately expressed) | $3.3 \times 10^{-8}$ | $3.3 \times 10^{-8}$ | 2.00E+01 | 0 |

The molecular library may be substituted for by synthetically produced chemicals. It would still be necessary to approximate the highest probable affinity of target chemicals in the "chemical library" to be isolated and the number concentration of each modified chemical compound added.

EXAMPLE 13

Using the Equations to Determine the Suitability of a Known Molecular Library in Performing the Invention The equations of the invention can be used to evaluate molecular libraries of known parameters (including of known amounts) for their suitability to isolate anti-ligands with a given specificity. E.g. use of the equations can determine the amount of subtractor and/or target ligand required to isolate the requisite binders and may be compared to the amounts known in a provided sample, in order to determine if a sufficient amount of ligand is present.

EXAMPLE 14

Performing the Invention by Automatic Methods

Screening of anti-ligands using the method of the invention may be performed using varying levels of automation. The determination of the amount of first subtractor and second target ligand can be performed using a computer program designed to run the equations derived from the law of mass action.

Furthermore the method of screening may be further automated if necessary for high throughput screening. In this situation, the automatic determination of the amount of first and second target ligands, is followed by automatically providing the determined amounts of first and second target ligands and automatically exposing the ligands to the anti-ligand.

An outline for a computer software program utilising the invention to automate the binder selection processes of the present invention. Is described below:

The user will be asked to choose a selection program. In "simple" mode such programs would include:
A. Positive to negative inter-population ligand abundance dependent analysis and positive intra-population ligand abundance independent isolation of binders (higher stringency-higher antigen concentrations needed). This program is ideal for biomarker or target discovery. (e.g. FIG. 5)
B. Positive to negative inter-population ligand abundance dependent analysis and positive population intra-population ligand abundance dependent isolation of binders (lower stringency-lower antigen concentrations needed) (e.g. FIG. 2). This program would have different subprograms, e.g. "transfected-cell selection", "wild-type cell selection", or "plasma selection". Depending on which type of selection is chosen the software program will estimate the relative frequencies of target ligands present at different absolute and relative numbers in the positive and negative ligand populations. The user may also choose to enter these numbers manually.

The user will be asked to specify which category of binders is of interest. The user may choose to perform selection such that only binders with specificity for positive population unique ligands are isolated, or choose to include binders with specificity for ligands present at higher concentration in the positive ligand population compared to the negative ligand population. The user will also provide information about the binder library:
1. Diversity of library (number of unique binders). This value is used to set higher threshold for binder affinity.
2. Library binder copy number—the multiplicity of each unique binder member
3. Selection reaction volume (litres)
4. Threshold for binder affinity (Kd (M))—This value is the lowest affinity of interest of any binder for its target ligand. The upper threshold for this value is determined from 1.
5. The expected number of times each binder will be multiplied following a selection round ("The amplification factor"). The amplification factor is calculated as the number of phage following amplification of binders isolated firm a given selection round divided by the number of binders isolated from the same selection round. The expected amplification factor is replaced by the actual amplification factor calculated as selection rounds are performed so that each selection round is optimised.
6. Lowest accepted number of unique binders isolated following each selection round. This number could be anything from less than 1 to the input binder copy number.
7. Availability of subtractor ligand constructs (the highest number of subtractor constructs that are available and may be used in the selection process)
8. "Ligand detection level". The approximate concentration of the lowest abundant target ligand of interest in the positive ligand population. Binders specific for target ligand present at lower concentrations than that specified here may not be expected to be isolated.
9. Desired frequency of binders with specificity for the most rare or weakly upregulated ligands isolated following the final round of selection.

Given the above parameters, the computer program will calculate the number of selection rounds necessary for binders with sought specificity and affinity to be isolated at desired frequency (based on entered parameter values), and the number of positive and negative ligand constructs to use in the selection rounds respectively. All or none of the parameters entered for a given selection may be saved and used for subsequent selections.

Furthermore, the output concerning the quantities of any material and the number of selection rounds can be linked through a software program to an automated experimental set-up where by the user inputting data allows the automatic calculation and implementation of the requisite experimental materials.

REFERENCES

Barbas C F, Kang A s, Lerner R A and Benkovic S J, (1991), Assembly of combinatorial antibody libraries on phage surfaces: the gene III site. *Proc. Natl. Acad. Sci. USA* 88, 7978-7982;

Carlsson, R., Fischer, H. and Sjogren, H. O. (1988) Binding of staphylococcal enterotoxin A to accessory cells is a requirement for its ability to activate human T cells. *J. Immunol* 140, 2484.

Chiswell D J and McCafferty J, (1992), Phage antibodies: will new 'coliclonal' antibodies replace monoclonal antibodies? *Trends Biotechnol.* 10, 80-84

Clackson T, Hoogenboom H R, Griffiths A D and Winter G, (1991), Making antibody fragments using phage display libraries. *Nature* 352, 624-628 de Kruif, J., Terstappen, L., Boel, E. and Logtenberg, T. (1995) Rapid selection of cell subpopulation-specific human monoclonal antibodies from a synthetic phage antibody library. *Proc Natl Acad Sci USA* 92, 3938.

Dower, W. J., CAVIRLA, S. E. and N. V., A. T. (1991) Recombinant Library Screening Methods. In: *World Intellectual Property Organization.* SMITH, W. M., United States.

Felici F, Luzzago A, Manaci P, Nicosia A, Sollazzo M and Traboni C, (1995), Peptide and protein display on the surface of filamentous bacteriophage. *Biotechnol. Annual Rev.* 1, 149-183

Francisco, J. A., Stathopoulos, C., Warren, R. A., Kilburn, D. G. and Georgiou, G. (1993) Specific adhesion and hydrolysis of cellulose by intact Escherichia coli expressing surface anchored cellulase or cellulose binding domains. *Biotechnology* (NY) 11, 491.

Gao, C., Lin, C. H., Lo, C. H., Mao, S., Wirsching, P., Lerner, R. A. and Janda, K. D. (1997) Making chemistry selectable by linking it to infectivity. *Proc Natl A cad Sci USA* 94, 11777.

Hanes, J. and Pluckthun, A. (1997) In vitro selection and evolution of functional proteins by using ribosome display. *Proc Natl Acad Sci USA* 94, 4937.

He, M. and Taussig, M. J. (1997) Antibody-ribosome-mRNA (ARM) complexes as efficient selection particles for in vitro display and evolution of antibody combining sites. *Nucleic Acids Res* 25, 5132.

Hoogenboom H R and Winter G, (1992), By-passing immunisation Human antibodies from synthetic repertoires of germline VH gene segments rearranged in vitro. *J. Mol. Biol.* 227, 381-388).

Hoogenboom H R, deBruine A P, Hutton S E, Hoet R M, Arends J W and Rooves R C, (1998)., Antibody phage display technology and its application. *Immunotechnology* 4(1), 1-20.

Hus, G. A., Heijnen, I. A., Cuomo, M. E., Koningsberger, J. C., Wiegman, L., Boel, E., van der Vuurst de Vries, A. R., Loyson, S. A., Helfrich, W., van Berge Henegouwen, C. P., van Meijer, M., de Kruif, J. and Logtenberg, T. (1999) A recombinant, fully human monoclonal antibody with anti-tumor activity constructed from phage-displayed antibody fragments. *Nat Biotechnology* 17, 276.

Jacobsson, K. and Frykberg, L. (1995) Cloning of ligand-binding domains of bacterial receptors by phage display. *Biotechniques* 18, 878.

Katz B A, (1997), Structural and mechanistic determinants of affinity and specificity of ligands discovered or engineered by peptide display. *Annual Rev. Biophys. Biomol. Struct.* 26, 27-45

Kay B K and Paul J I, (1996), High-throughput screening strategies to identify inhibitors of protein-protein interactions. *Mol. Divers.* 1, 139-140).

Koide, A., Bailey, C. W., Huang, X. and Koide, S. (1998) The fibronectin type III domain as a scaffold for novel binding proteins. *J Mol Biol* 284, 1141.

Mandecki, W., Chen, Y. C. J. and Girhalde N (1995) A mathematical model fro biopanning (affinity selection) using peptide libraries on filamentous phage. *J. theor. Biol.* 176, pp 523-530

Markland, W., Roberts, B. L., Saxena, M. J., Guterman, S. K. and Ladner, R. C. (1991) Design, construction and function of a multicopy display vector using fusions to the major coat protein of bacteriophage M13. *Gene* 109, 13.

Marks J D, Hoogenboom H R, Bonnert T P, McCafferty J, Griffiths A D and Winter G, (1991), By-passing immunisation. Human antibodies from V-gene libraries displayed on phage. *J. Mol. Biol.* 222, 581-597

Mattheakis, L. C., Bhatt, R. R. and Dower, W. J. (1994) An in vitro polysome display system for identifying ligands from very large peptide libraries. *Proc Natl Acad Sci USA* 91, 9022.

McCafferty, J., Griffiths, A. D., Winter, G. and Chiswell, D. J. (1990) Phage antibodies: filamentous phage displaying antibody variable domains. *Nature* 348, 552.

Siegel, D. L., Chang, T. Y., Russell, S. L. and Bunya, V. Y. (1997) Isolation of cell surface-specific human monoclonal antibodies using phage display and magnetically-activated cell sorting: applications in immunohematology. *J Immunol Methods* 206, 73.

Smith, G. P. (1985) Filamentous fusion phage: novel expression vectors that display cloned antigens on the virion surface. *Science* 228, 1315.

Smith, G. P. and Scott, J. K. (1993) Libraries of peptides and proteins displayed on filamentous phage. *Methods Enzymol* 217, 228.

Stahl, S., Sjolander, A., Nygren, P. A., Berzins, K., Perlmann, P. and Uhlen, M. (1989) A dual expression system for the generation, analysis and purification of antibodies to a repeated sequence of the Plasmodium falciparum antigen Pf155/RESA. *J Immunol Methods* 124, 43.

Stausbøl-Grøn, B., Wind, T., Kjaer, S., Kahns, L., Hansen, N., Kristensen, P., and Clark, B. (1996) A model phage display subtraction method with potential for analysis of differential gene expression. *Febs Letters,* 391, pp 71-75

Stausbøl-Grøn, B., Jensen, K. B., Jensen, K. H., Jensen, M. and Clark, B. (2001) De novo identification of cell-type specific antibody-antigen pairs by phage display subtraction, *Eur. J. Biochem.,* 268, 3099-3107

Weng, S., Gu, K., Hammond, P. W., Lohse, P., Rise, C., Wagner, R. W., Wright, M. C. and Kuimelisa, R. G. (2002) Generating addressable protein microarrays with PROfusion covalent mRNA-protein fusion technology. *Proteomics* 2, 48.

Williams, B. R. and Sharon, J. (2002) Polyclonal anti-colorectal cancer Fab phage display library selected in one round using density gradient centrifugation to separate antigen-bound and free phage. *Immunol Lett* 81, 141.

Winter, G., Griffiths, A. D., Hawkins, R. E. and Hoogenboom, H. R. (1994) Making antibodies by phage display technology. *Annu Rev Immunol* 12, 433.

Winter and McCafferty (1996) *Phage display of peptides and proteins: a laboratory manual* Ed Kay, Academic Press, Inc ISBN 0-12-402380-0

The invention claimed is:

1. A method of isolating at least one anti-ligand to at least one differentially expressed target ligand comprising the steps of:
   (i) providing a library of anti-ligands;
   (ii) providing a population of subtractor ligand constructs, said subtractor ligand constructs comprising a ligand associated with a separation means, wherein said separation means is a physical feature of the subtractor ligand construct;
   (iii) providing a population of target ligand constructs, said target ligand constructs comprising the same ligand as step (ii) associated with a separation means, wherein said separation means is a physical feature of the target ligand construct;
   (iv) determining the amounts of subtractor ligand construct and target ligand construct utilizing one or more equations derived from the universal law of mass action $$\frac{[C]^c [d]^d}{[A]^a [B]^b} = K_{eq},$$

where:
   A, B, C & D=are the participants in the reaction (reactants and products)
   a, b, c, & d=the coefficients necessary for a balanced chemical equation to permit the determination of the amount of subtractor ligand as compared to target ligand required for isolation of at least one anti-ligand to at least one target ligand;
   (v) providing the amount of the subtractor ligand construct determined in step (iv);
   (vi) providing the amount of the target ligand construct determined in step (iv);
   (vii) exposing the anti-ligand library of (i) to the amounts of subtractor ligand construct provided in step (v) and the amounts of the target ligand construct provided in step (vi) to permit binding of anti-ligands to ligands; and
   (viii) isolating the anti-ligand bound to the target ligand construct.

2. The method of claim 1 further comprising the step of separating the anti-ligand bound to the ligand of the target ligand construct.

3. The method of claim 1 wherein steps (ii) to (viii) are repeated one or more times.

4. The method of claim 1 wherein the amount of one of the subtractor ligand construct or target ligand construct is provided in excess of the amount of the other of the subtractor ligand construct or the target ligand construct.

5. The method of claim 4 where the excess of either the target ligand construct or the subtract ligand construct is 10 to 100 fold.

6. The method of claim 1 wherein the equation of (iv) is $$bA = \frac{(A + T + (K_d) \times (C \times V))}{2} - \sqrt{\frac{(A + T + (K_d) \times (C \times V))^2}{4} - A \times T}$$

where
bA=Bound anti-ligand
A=Total number of anti-ligand
T=Total number of ligands of both the target ligand construct and the subtractor ligand construct
C=Avogadro's constant (6.022×10²³ particles/mole)
V=Reaction volume (liters)
$K_d$=Equilibrium dissociation constant.

7. The method of claim 1 wherein the equation of (iv) is:

$$bA = \left\{ \frac{(A + T + (K_d) \times (C \times V))}{2} - \sqrt{\frac{(A + T + (K_d) \times (C \times V))^2}{4} - A \times T} \right\} \times \left\{ \frac{(T_p \times C_p)}{((T_p \times C_p) + (T_s \times C_s))} \right\}$$

where
$bA_p$=Bound anti-ligand
$T_p$=The number of ligands of the target ligand constructs on $C_p$
$T_s$=The number of ligands of the subtractor ligand constructs on $C_s$
$C_p$=The number of target ligand constructs
$C_s$=The number of subtractor ligand constructs
A=Total number of anti-ligand
T=Total number of ligands of both target ligand constructs and subtractor ligand constructs
C=Avogadro's constant (6.022×10²³ particles/mole)
V=Reaction volume (liters)
$K_d$=Equilibrium dissociation constant.

8. The method of claim 1 wherein the separation means is selected from the group consisting of at least one of a solid support, cell membrane and/or portions thereof, synthetic membrane, beads, and/or chemical tags.

9. The method of claim 8 wherein the separation means is cell membranes and/or portions thereof.

10. The method of 9 whereby the subtractor and target ligands are fixed to and/or incorporated within separate cell membranes and/or portions thereof.

11. The method of claim 1 whereby the separation means of the subtractor and target ligand constructs have a different density.

12. The method of claim 11 wherein the separation means of the subtractor ligand construct is of a lower density than the separation means of the target ligand construct.

13. The method of claim 12 wherein the separation means of the subtractor ligand construct is a membrane vesicle.

14. The method of claim 12 wherein the separation means of the target ligand construct is a whole cell membrane.

15. The method of claim 1 wherein the isolating of step (viii) is performed using at least one method selected from the group consisting of density centrifugation, solid support sequestration, magnetic bead sequestration, chemical tag binding and/or aqueous phase partitioning.

16. The method of claim 15 wherein the isolating of step (viii) is performed by density centrifugation.

17. The method of claim 16 wherein the density centrifugation utilizes a sucrose-polymer gradient.

18. The method of claim 1 wherein the library of step (i) is a display library comprising a plurality of library members which display anti-ligands.

19. The method of claim 18 wherein the library is a phage display library.

20. The method of claim 1 wherein the subtractor and target ligands are independently selected from the group consisting of at least one of (i) antigens; (ii) receptor ligands; and/or (iii)

enzyme targets selected from the group consisting of a carbohydrate; protein; peptide; lipid; polynucleotide; inorganic molecules and/or conjugated molecules.

21. The method of claim 1 wherein the library of anti-ligands comprises one or more of the following: antibodies, and/or antigen binding variants, derivatives or fragments thereof; scaffold molecules with engineered variable surfaces; receptors; and/or enzymes.

22. The method of claim 1 comprising a further step of exposing the ligand of the target ligand construct to a stimulus which influences the expression of said target ligand construct.

* * * * *

UNITED STATES PATENT AND TRADEMARK OFFICE
CERTIFICATE OF CORRECTION

PATENT NO. : 8,592,347 B2  Page 1 of 1
APPLICATION NO. : 10/526695
DATED : November 26, 2013
INVENTOR(S) : Björn Frendéus It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2158 days.

Signed and Sealed this
Twenty-second Day of September, 2015

Michelle K. Lee
*Director of the United States Patent and Trademark Office*